(12) United States Patent
Sen et al.

(10) Patent No.: US 12,108,992 B2
(45) Date of Patent: Oct. 8, 2024

(54) SYSTEMS AND METHODS FOR TRACKING A POSITION OF A ROBOTICALLY-MANIPULATED SURGICAL INSTRUMENT

(71) Applicant: Intuitive Surgical Operations, Inc., Sunnyvale, CA (US)

(72) Inventors: Siddarth Sen, San Jose, CA (US); Brian D. Hoffman, Mountain View, CA (US); Geoffrey A. Richmond, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 926 days.

(21) Appl. No.: 17/264,257

(22) PCT Filed: Jul. 27, 2019

(86) PCT No.: PCT/US2019/043825
§ 371 (c)(1),
(2) Date: Jan. 28, 2021

(87) PCT Pub. No.: WO2020/028202
PCT Pub. Date: Feb. 6, 2020

(65) Prior Publication Data
US 2021/0290317 A1    Sep. 23, 2021

Related U.S. Application Data

(60) Provisional application No. 62/712,368, filed on Jul. 31, 2018.

(51) Int. Cl.
*A61B 34/20* (2016.01)
*A61B 34/00* (2016.01)
*G06N 3/047* (2023.01)

(52) U.S. Cl.
CPC .............. *A61B 34/20* (2016.02); *A61B 34/70* (2016.02); *G06N 3/047* (2023.01); *A61B 2034/2065* (2016.02)

(58) Field of Classification Search
CPC . A61B 34/20; A61B 34/70; A61B 2034/2065; G06N 3/047
See application file for complete search history.

(56) References Cited

U.S. PATENT DOCUMENTS

| 2008/0071142 A1 | 3/2008 | Gattani et al. |
| 2009/0088897 A1 | 4/2009 | Zhao et al. |

(Continued)

FOREIGN PATENT DOCUMENTS

| CN | 104244800 A | 12/2014 |
| CN | 106535805 A | 3/2017 |

(Continued)

OTHER PUBLICATIONS

International Search Report and Written Opinion for Application No. PCT/US2019/043825, mailed on Oct. 29, 2019, 14 pages.

(Continued)

*Primary Examiner* — David Perlman

(57) ABSTRACT

An exemplary surgical instrument tracking system includes at least one physical computing device that determines, based on endoscopic imagery of a surgical area and using a trained neural network, an observation for an object of interest depicted in the endoscopic imagery, associates, based on a probabilistic framework and kinematics of a robotically-manipulated surgical instrument located at the surgical area, the observation for the object of interest to the robotically-manipulated surgical instrument, and determines a physical position of the robotically-manipulated surgical instrument at the surgical area based on the kinematics of the robotically-manipulated surgical instrument and the obser- (Continued)

vation associated with the robotically-manipulated surgical instrument.

20 Claims, 18 Drawing Sheets

(56) References Cited

U.S. PATENT DOCUMENTS

| | | | |
|---|---|---|---|
| 2010/0298641 A1* | 11/2010 | Tanaka | A61B 1/04 600/109 |
| 2014/0275985 A1* | 9/2014 | Walker | A61B 5/062 606/130 |
| 2015/0297313 A1* | 10/2015 | Reiter | A61B 5/7267 600/408 |

FOREIGN PATENT DOCUMENTS

| | | |
|---|---|---|
| CN | 107049492 A | 8/2017 |
| JP | 5280620 B2 | 9/2013 |
| WO | WO-2008002830 A2 | 1/2008 |
| WO | WO-2014093824 A1 | 6/2014 |
| WO | WO-2016149345 A1 | 9/2016 |

OTHER PUBLICATIONS

Jin A., et al., "Tool Detection and Operative Skill Assessment in Surgical Videos Using Region-Based Convolutional Neural Networks," IEEE Winter Conference on Applications of Computer Vision (WACV), Mar. 2018, pp. 691-699.

Reiter A., et al., "Marker-less Articulated Surgical Tool Detection," Computer Assisted Radiology and Surgery, Jun. 2012, XP055278638, pp. 1-8.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

International Preliminary Report on Patentability for Application No. PCT/US2019/043825, mailed on Feb. 11, 2021, 10 pages.

* cited by examiner

SYSTEMS AND METHODS FOR TRACKING A POSITION OF A ROBOTICALLY-MANIPULATED SURGICAL INSTRUMENT

RELATED APPLICATIONS

The present application claims priority to International Application No. PCT/US2019/043825, filed on Jul. 27, 2019, and entitled "Systems and Methods for Tracking a Position of a Robotically-Manipulated Surgical Instrument," which claims priority to U.S. Provisional Patent Application No. 62/712,368, filed on Jul. 31, 2018, and entitled "Systems and Methods for Tracking a Position of a Robotically-Manipulated Surgical Instrument." The contents of these applications are hereby incorporated by reference in their entirety.

BACKGROUND INFORMATION

A robotic surgical system allows a surgeon to control robotically-manipulated surgical instruments to perform a surgical procedure on a patient. For a minimally-invasive surgery, for example, robotically-manipulated surgical instruments are inserted into a patient through one or more cannulas. The surgical instruments typically include an endoscope that captures images of a surgical area and one or more surgical tools that are robotically manipulated by the robotic surgical system to perform a surgical procedure. A surgeon views the endoscopic images of the surgical area and uses master controls of the robotic surgical system to control movement of the robotically-manipulated surgical instruments to perform the surgical procedure.

Tracking positions of robotically-manipulated surgical instruments within a surgical area is an important component of a robotic surgical system. However, such tracking of surgical instrument position by a robotic surgical system is technically challenging, particularly when a certain level of precision, accuracy, efficiency, and/or reliability is desired.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
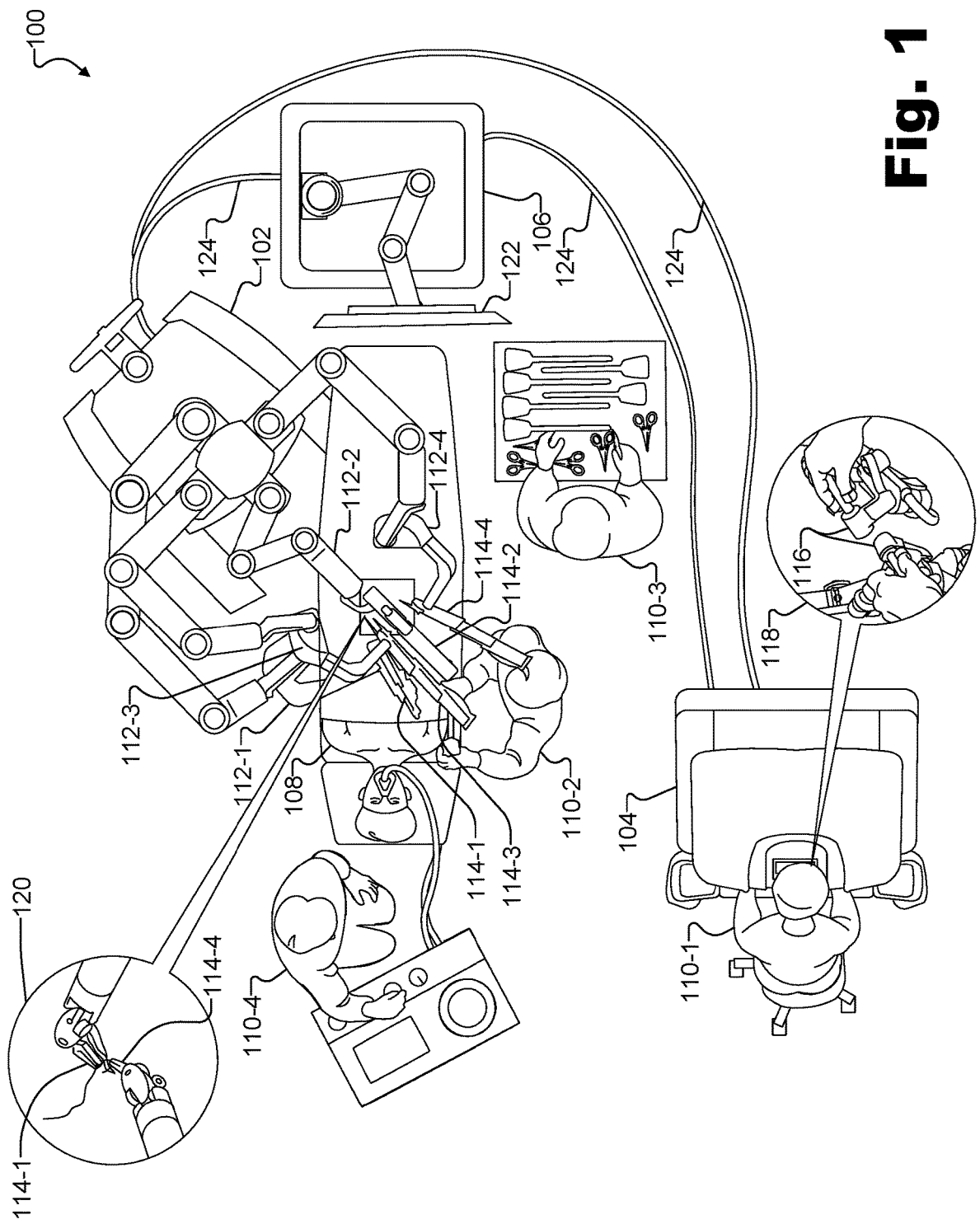
FIG. 1 illustrates an exemplary robotic surgical system according to principles described herein.

Systems and methods for tracking a position of a robotically-manipulated surgical instrument are described herein. As will be described in more detail below, in certain implementations, an exemplary surgical instrument tracking system may be configured to determine, based on endoscopic imagery of a surgical area and using a trained neural network, an observation for an object of interest depicted in the endoscopic imagery, associate, based on a probabilistic framework and kinematics of a robotically-manipulated surgical instrument located at the surgical area, the observation for the object of interest to the robotically-manipulated surgical instrument, and determine a physical position of the robotically-manipulated surgical instrument at the surgical area based on the kinematics of the robotically-manipulated surgical instrument and the observation associated with the robotically-manipulated surgical instrument.

As will also be described in more detail herein, in certain implementations, an exemplary surgical instrument tracking system may be configured to determine, based on endoscopic imagery of a surgical area and using a trained neural network, an observation for an object of interest depicted in the endoscopic imagery, and associate, based on kinematics of a robotically-manipulated surgical instrument located at the surgical area, the observation for the object of interest to the robotically-manipulated surgical instrument or to a false positive designation. When the observation for the object of interest is associated with the robotically-manipulated surgical instrument, the surgical instrument tracking system may determine a physical position of the robotically-manipulated surgical instrument at the surgical area based on the kinematics of the robotically-manipulated surgical instrument and the observation associated with the robotically-manipulated surgical instrument. When the observation for the object of interest is associated with the false positive designation, the surgical instrument tracking system may refrain from using the observation to determine the physical position of the robotically-manipulated surgical instrument at the surgical area.

As used herein, the position of an instrument can refer to a three-dimensional ("3D") location and/or orientation of a desired portion of the instrument, such as an end effector (e.g., jaws, shears, etc.), a distal tool tip, a wrist, a shaft, and/or another structural component of the instrument. For example, the position of an instrument can refer to a 3D location and/or orientation of a component of the instrument within a 3D space, such as a 3D space defined by a 3D coordinate system.

By determining a physical position of a robotically-manipulated surgical instrument as described herein, exemplary surgical instrument tracking systems and methods may track surgical instrument position with precision, accuracy, efficiency, and/or reliability at a level that facilitates one or more features, benefits, and/or advantages of a robotic surgical system. In certain implementations, such precision, accuracy, efficiency, and/or reliability may be provided by an exemplary surgical instrument tracking system without using dedicated computer vision markers on surgical instruments (e.g., bar codes, colors, patterns, etc. integrated on or otherwise attached to surgical instruments), which may be referred to as "marker-less" tracking of surgical instruments. In certain implementations, such precision, accuracy, efficiency, and/or reliability may be provided by an exemplary surgical instrument tracking system in real time or near real time using finite computing resources.

Various embodiments will now be described in more detail with reference to the figures. The systems and methods described herein may provide one or more of the benefits mentioned above and/or various additional and/or alternative benefits that will be made apparent herein.

The surgical instrument tracking systems and methods described herein may operate as part of or in conjunction with a robotic surgical system. As such, in order to promote an understanding of the surgical instrument tracking systems and methods described herein, an exemplary robotic surgical system will now be described. The described exemplary robotic surgical system is illustrative and not limiting. The surgical instrument tracking systems and methods described herein may operate as part of or in conjunction with other suitable robotic surgical systems.

FIG. 1 illustrates an exemplary robotic surgical system 100. As shown, robotic surgical system 100 may include a patient-side system 102 (sometimes referred to as a patient-side cart), a surgeon console 104, and a vision cart 106 communicatively coupled one to another. Robotic surgical system 100 may be utilized by a surgical team to perform a robotically-enabled surgical procedure on a patient 108. As shown, the surgical team may include a surgeon 110-1, an assistant 110-2, a nurse 110-3, and an anesthesiologist 110-4, all of whom may be collectively referred to as "surgical team members 110." Additional or alternative surgical team members may be present during a surgical session as may serve a particular implementation. While FIG. 1 illustrates an ongoing minimally invasive surgical procedure, it will be understood that robotic surgical system 100 may similarly be used to perform open surgical procedures or other types of surgical procedures that may similarly benefit from robotic surgical system 100. Additionally, it will be understood that the surgical session throughout which robotic surgical system 100 may be employed may not only include an operative phase of a surgical procedure such as illustrated in FIG. 1, but may also include preoperative, postoperative, and/or other suitable phases of the surgical procedure.

As shown, patient-side system 102 may include a plurality of robotic arms 112 (e.g., robotic arms 112-1 through 112-4) to which a plurality of robotically-manipulated surgical instruments 114 (e.g., surgical instruments 114-1 through 114-4) may be coupled. Each surgical instrument 114 may include any suitable surgical tool, medical tool, monitoring instrument (e.g., an endoscope), diagnostic instrument, or the like that may be used for a robotically-enabled surgical procedure on patient 108 (e.g., by being at least partially inserted into patient 108 and manipulated to perform a robotically-enabled surgical procedure on patient 108). Note that while patient-side system 102 is depicted and described herein as a cart with a plurality of robotic arms 112 for exemplary purposes, in various other embodiments patient-side system 102 can include one or more carts, each with one or more robotic arms 112, one or more robotic arms 112 mounted on a separate structure within the operating room such as the operating table or the ceiling, and/or any other support structure(s). Patient-side system 102 will be described in more detail below.

Surgical instruments 114 may each be positioned at a surgical area associated with a patient. As used herein, a "surgical area" associated with a patient may, in certain examples, be entirely disposed within the patient and may include an area within the patient near where a surgical procedure is planned to be performed, is being performed, or has been performed. For example, for a minimally invasive surgical procedure being performed on tissue internal to a patient, the surgical area may include the tissue as well as space around the tissue where, for example, surgical instruments being used to perform the surgical procedure are located. In other examples, a surgical area may be at least partially disposed external to the patient. For instance, robotic surgical system 100 may be used to perform an open surgical procedure such that part of the surgical area (e.g., tissue being operated on) is internal to the patient while another part of the surgical area (e.g., a space around the tissue where one or more surgical instruments may be disposed) is external to the patient. A surgical instrument (e.g., any of surgical instruments 114) may be referred to as being "located at" (or "located within") a surgical area when at least a portion of the surgical instrument (e.g., a distal end of the surgical instrument) is disposed within the surgical area.

Surgeon console 104 may be configured to facilitate control by surgeon 110-1 of robotic arms 112 and surgical instruments 114. For example, surgeon console 104 may provide surgeon 110-1 with imagery (e.g., high-definition 3D imagery) of a surgical area associated with patient 108 as captured by an endoscope. Surgeon 110-1 may utilize the imagery to perform one or more procedures with surgical instruments 114.

To facilitate control of surgical instruments 114, surgeon console 104 may include a set of master controls 116 (shown in close-up view 118). Master controls 116 may be manipulated by surgeon 110-1 in order to control movement of surgical instruments 114. Master controls 116 may be configured to detect a wide variety of hand, wrist, and finger movements by surgeon 110-1. In this manner, surgeon 110-1 may intuitively perform a procedure using one or more of surgical instruments 114. For example, as depicted in close-up view 120, functional tips of surgical instruments 114-1 and 114-4 coupled to robotic arms 112-1 and 112-4, respectively, may mimic the dexterity of the hand, wrist, and fingers of surgeon 110-1 across multiple degrees of freedom of motion in order to perform one or more surgical procedures (e.g., an incision procedure, a suturing procedure, etc.). Although surgeon console 104 is depicted and described herein as a single unit for exemplary purposes, in various other embodiments surgeon console 104 can include a variety of discrete components, such as wired or wireless master controls 116, a separate display element(s) (e.g., a projector or head-mounted display), separate data/communications processing hardware/software, and/or any other structural or functional elements of surgeon console 104. Surgeon console 104 will be described in more detail below.

Vision cart 106 may be configured to present visual content to surgical team members 110 who may not have access to the images provided to surgeon 110-1 at surgeon console 104. To this end, vision cart 106 may include a display monitor 122 configured to display one or more user interfaces, such as images (e.g., 2D images) of the surgical area, information associated with patient 108 and/or the surgical procedure, and/or any other visual content as may serve a particular implementation. For example, display monitor 122 may display images of the surgical area together with additional content (e.g., graphical content, contextual information, etc.) overlaid on top of or otherwise concurrently displayed with the images. In some embodiments, display monitor 122 is implemented by a touchscreen display with which surgical team members 110 may interact (e.g., by way of touch gestures) to provide user input to robotic surgical system 100.

Patient-side system 102, surgeon console 104, and vision cart 106 may be communicatively coupled one to another in any suitable manner. For example, as shown in FIG. 1, patient-side system 102, surgeon console 104, and vision cart 106 may be communicatively coupled by way of control lines 124, which may represent any wired or wireless communication link as may serve a particular implementation. To this end, patient-side system 102, surgeon console 104, and vision cart 106 may each include one or more wired or wireless communication interfaces, such as one or more local area network interfaces, Wi-Fi network interfaces, cellular interfaces, etc.

Patient-side system 102, surgeon console 104, and vision cart 106 may each include at least one computing device configured to control, direct, and/or facilitate operations of robotic surgical system 100. For example, surgeon console 104 may include a computing device configured to transmit instructions by way one or more of control lines 124 to patient-side system 102 in order to control movement of robotic arms 112 and/or surgical instruments 114 in accordance with manipulation by surgeon 110-1 of master controls 116. In some examples, vision cart 106 may include one or more computing devices configured to perform primary processing operations of robotic surgical system 100. In such configurations, the one or more computing devices included in vision cart 106 may control and/or coordinate operations performed by various other components (e.g., by patient-side system 102 and/or surgeon console 104) of robotic surgical system 100. For example, a computing device included in surgeon console 104 may transmit instructions to patient-side system 102 by way of the one or more computing devices included in vision cart 106.

Figure 2:
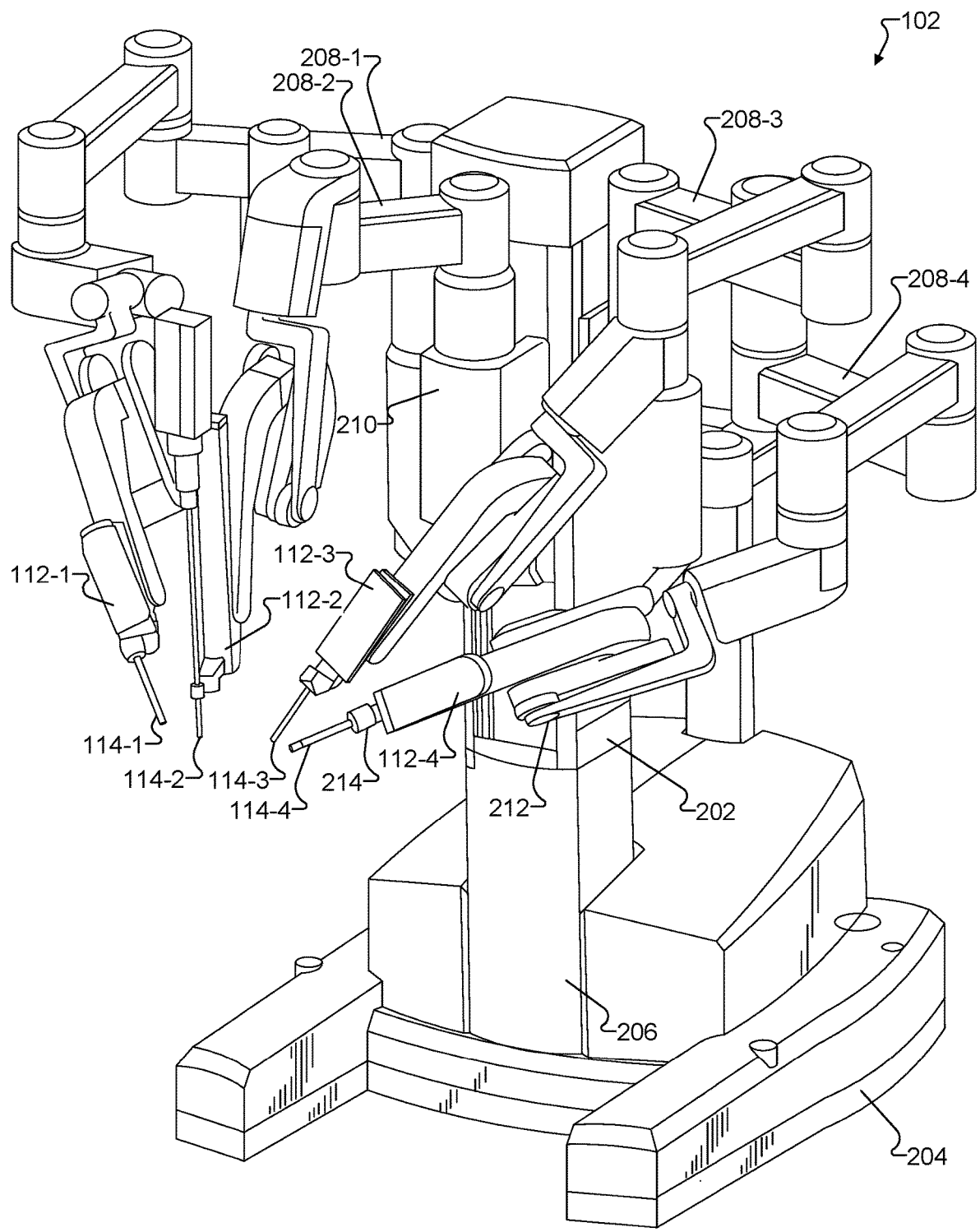
FIG. 2 illustrates an exemplary patient-side system included within the robotic surgical system of FIG. 1 according to principles described herein.

FIG. 2 illustrates a perspective view of patient-side system 102. As shown, patient-side system 102 includes a cart column 202 supported by a base 204. In some examples, cart column 202 may include a protective cover 206 that protects components of a counterbalance subsystem and a braking subsystem disposed within cart column 202 from contaminants.

Cart column 202 may support a plurality of setup arms 208 (e.g., setup arms 208-1 through 208-4) mounted thereon. Each setup arm 208 may include a plurality of links and joints that allow manual positioning of setup arms 208, and may each be connected to one of robotic arms 112. In the example of FIG. 2, patient-side system 102 includes four setup arms 208 and four robotic arms 112. However, it will be recognized that patient-side system 102 may include any other number of setup arms 208 and robotic arms 112 as may serve a particular implementation.

Setup arms 208 may be non-robotically controllable and configured to statically hold each robotic arm 112 in a respective position desired by a person setting up or reconfiguring patient-side system 102. Setup arms 208 may be coupled to a carriage housing 210 and manually moved and situated during a preoperative, operative, or postoperative phase of a surgical session. For example, setup arms 208 may be moved and situated during a preoperative phase when robotic surgical system 100 is being prepared and/or targeted for a surgical procedure to be performed. In contrast, robotic arms 112 may be robotically controlled (e.g., in response to manipulation of master controls 116, as described above).

As shown, each robotic arm 112 may have a surgical instrument 114 coupled thereto. In certain examples, three of the four robotic arms 112 may be configured to move and/or position surgical instruments 114 in the form of surgical tools that are used to manipulate patient tissue and/or other objects (e.g., suturing materials, patching materials, etc.) within the surgical area. Specifically, as shown, robotic arms 112-1, 112-3, and 112-4 may be used, respectively, to move and/or position surgical instruments 114-1, 114-3, and 114-4. A fourth robotic arm 112 (e.g., robotic arm 112-2 in the example of FIG. 2) may be used to move and/or position a monitoring instrument (e.g., a stereoscopic endoscope), as will be described in more detail below.

Robotic arms 112 may each include one or more displacement transducers, orientational sensors, and/or positional sensors (e.g., sensor 212) used to generate raw (i.e., uncorrected) kinematics information to assist in control and tracking of surgical instruments 114. For example, kinematics information generated by the transducers and the sensors in patient-side system 102, such as a kinematics-based position or other kinematics information for a robotic arm 112, may be transmitted to a surgical instrument tracking system of robotic surgical system 100 (e.g., a computing device included in vision cart 106). Each surgical instrument 114 may similarly include a displacement transducer, a positional sensor, and/or an orientation sensor (e.g., sensor 214) in certain implementations, each of which may provide additional kinematics information, such as a kinematics-based position or other kinematics information for a surgical instrument 114, to the tracking system. The tracking system may process the kinematics information received from the sensors included on robotic arms 112 and/or surgical instruments 114 to perform various operations, such as determining physical positions of robotic arms 112 and/or surgical instruments 114 as described herein.

Figure 3:
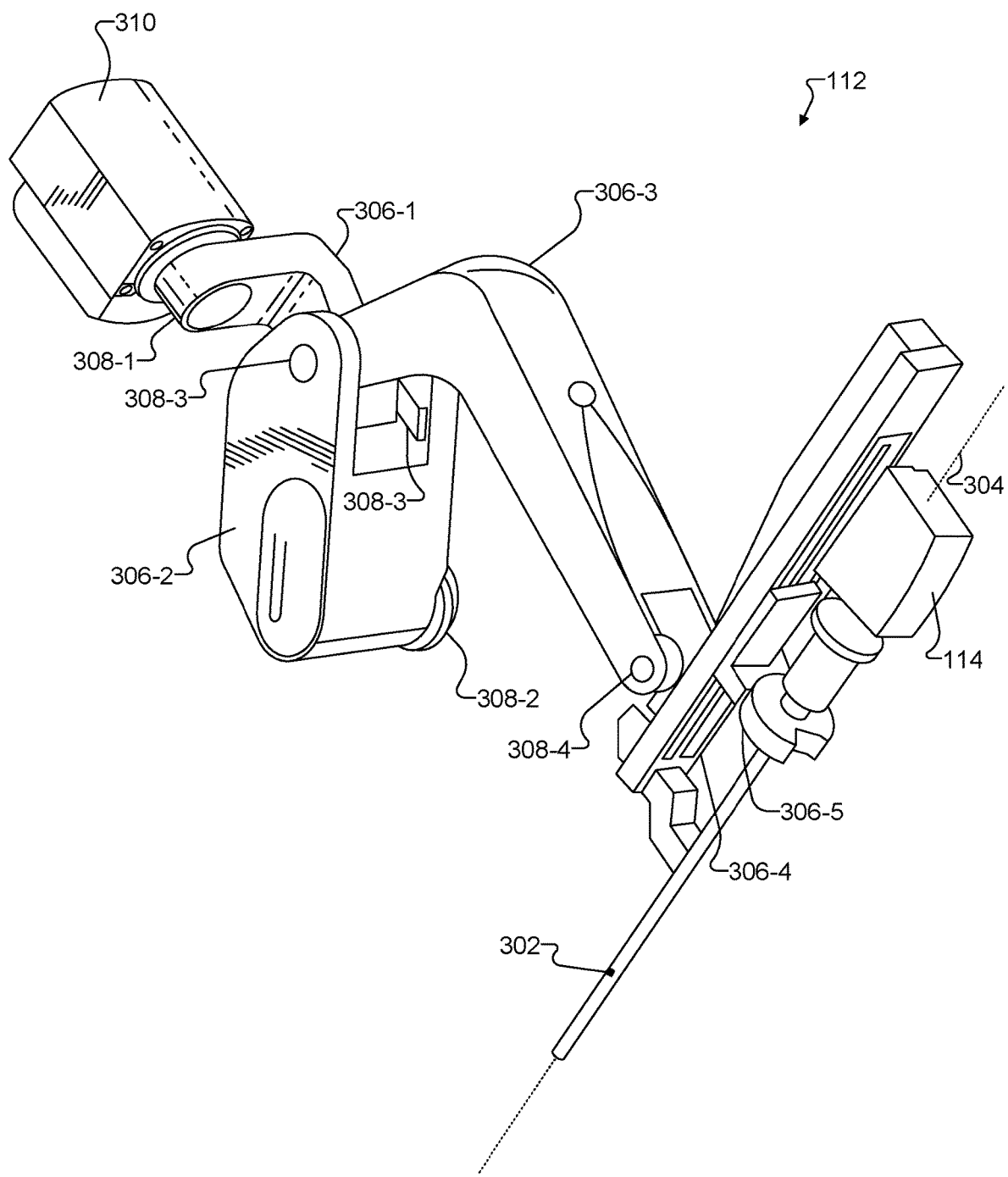
FIG. 3 illustrates an exemplary robotic arm included within the patient-side system of FIG. 2 according to principles described herein.

FIG. 3 illustrates a perspective view of an exemplary robotic arm 112 (e.g., any one of robotic arms 112-1 through 112-4). As shown, a surgical instrument 114 may be removably coupled to robotic arm 112. In the example of FIG. 3, surgical instrument 114 is an endoscopic device (e.g., a stereo laparoscope, an arthroscope, a hysteroscope, or another type of stereoscopic or monoscopic endoscope). Alternatively, surgical instrument 114 may be a different type of imaging device (e.g., an ultrasound device, a fluoroscopy device, an MRI device, etc.), a grasping instrument (e.g., forceps), a needle driver (e.g., a device used for suturing), an energy instrument (e.g., a cautery instrument, a laser instrument, etc.), a retractor, a clip applier, a probe grasper, a cardiac stabilizer, or any other suitable instrument or tool.

In some examples, it may be desirable for robotic arm 112 and surgical instrument 114 coupled to robotic arm 112 to move around a single fixed center point 302 so as to constrain movement of center point 302. For example, center point 302 may be located at or near a point of insertion of a surgical instrument 114 into patient 108. In certain surgical sessions (e.g., a surgical session associated with a laparoscopic surgical procedure), for instance, center point 302 may be aligned with an incision point to the internal surgical site by a trocar or cannula at an abdominal wall. As shown, center point 302 may be located on an insertion axis 304 associated with surgical instrument 114.

Robotic arm 112 may include a plurality of links 306 (e.g., links 306-1 through 306-5) pivotally coupled in series at a plurality of joints 308 (e.g., joints 308-1 through 308-4) near respective ends of links 306. For example, as shown, link 306-1 is pivotally coupled to a drive mount 310 at joint 308-1 near a first end of link 306-1, while being pivotally coupled to link 306-2 at joint 308-2 near a second end of link 306-1. Link 306-3 is pivotally coupled to link 306-2 near a first end of link 306-3 while being pivotally coupled to link 306-4 at joint 308-4 near a second end of link 306-3. Generally, link 306-4 may be substantially parallel to insertion axis 304 of surgical instrument 114, as shown. Link 306-5 is slidably coupled to link 306-4 to allow surgical instrument 114 to mount to and slide along link 306-5 as shown.

Robotic arm 112 may be configured to mount to a setup arm 208 (or a joint connected thereto) by way of drive mount 310 so as to be supported and held in place by setup arm 208, as described above. Drive mount 310 may be pivotally coupled to link 306-1 and may include a first internal motor (not explicitly shown) configured to yaw robotic arm 112 about a yaw axis of center point 302. In like manner, link 306-2 may house a second internal motor (not explicitly shown) configured to drive and pitch the linkage of robotic arm 112 about a pitch axis of center point 302. Likewise, link 306-4 may include a third internal motor (not explicitly shown) configured to slide link 306-5 and surgical instrument 114 along insertion axis 304. Robotic arm 112 may include a drive train system driven by one or more of these motors in order to control the pivoting of links 306 about joints 308 in any manner as may serve a particular implementation. As such, if surgical instrument 114 is to be mechanically moved, one or more of the motors coupled to the drive train may be energized to move links 306 of robotic arm 112.

Figure 4:
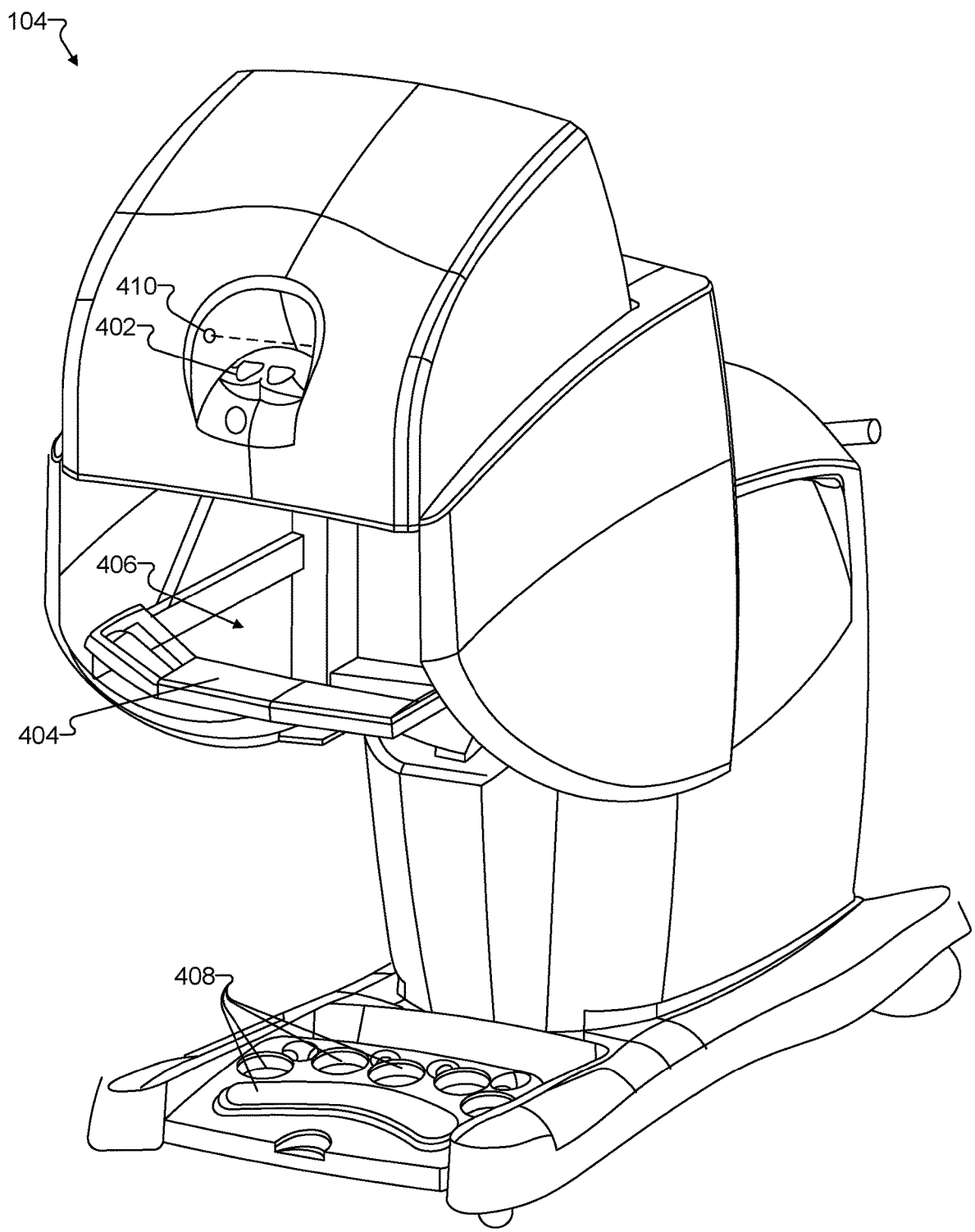
FIG. 4 illustrates an exemplary surgeon console included within the robotic surgical system of FIG. 1 according to principles described herein.

FIG. 4 illustrates a perspective view of surgeon console 104. As shown, surgeon console 104 may include a stereo viewer 402, an arm support 404, a controller workspace 406 within which master controls 116 (not shown in FIG. 4) are disposed, foot pedals 408, and a head sensor 410.

In some examples, stereo viewer 402 has two displays where stereoscopic images of a surgical area associated with patient 108 and generated by a stereoscopic endoscope may be viewed by an operator (e.g., surgeon 110-1) during a surgical session. When using surgeon console 104, the operator may move his or her head into alignment with stereo viewer 402 to view the stereoscopic images of the surgical area. To ensure that the operator is viewing the surgical area when controlling surgical instruments 114 of patient-side system 102, surgeon console 104 may use head sensor 410 disposed adjacent stereo viewer 402. Specifically, when the operator aligns his or her eyes with the binocular eye pieces of stereo viewer 402 to view a stereoscopic image of the surgical area, the operator's head may activate head sensor 410, which enables control of surgical instruments 114 by way of master controls 116. When the operator's head is removed from the area of stereo viewer 402, head sensor 410 may be automatically deactivated, which may prevent control of surgical instruments 114 by way of master controls 116. In this way, the position of surgical instruments 114 may remain static when robotic surgical system 100 detects that an operator is not actively engaged in attempting to control surgical instruments 114.

Arm support 404 may be used to support the elbows and/or forearms of the operator while he or she manipulates master controls 116 in order to control robotic arms 112 and/or surgical instruments 114. Additionally, the operator may use his or her feet to control foot pedals 408. Foot pedals 408 may be configured to change the configuration or operating mode of robotic surgical system 100, to generate additional control signals used to control surgical instruments 114, to facilitate switching control from one surgical instrument 114 to another, or to perform any other suitable operation.

Figure 5:
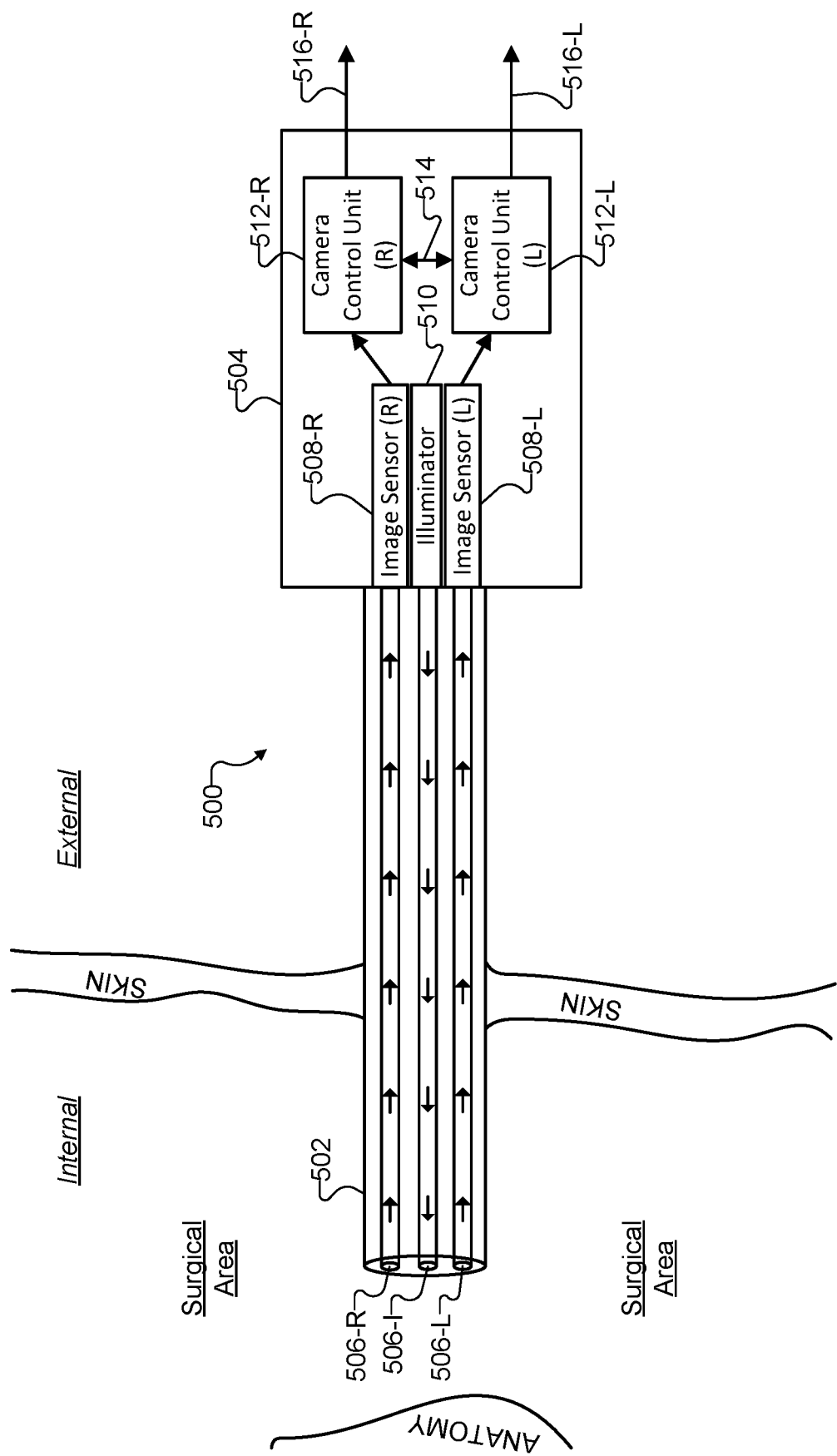
FIG. 5 illustrates an exemplary stereoscopic endoscope located at an exemplary surgical area associated with a patient according to principles described herein.

FIG. 5 illustrates an exemplary stereoscopic endoscope 500 included within robotic surgical system 100 and located at an exemplary surgical area associated with a patient. Stereoscopic endoscope 500 may be any one of surgical instruments 114 described above.

As shown, stereoscopic endoscope 500 may include a tube 502 having a distal tip that is configured to be inserted into a patient and a camera head 504 configured to be located external to the patient. Tube 502 may be coupled at a proximal end to camera head 504 and may be rigid (as shown in FIG. 5), jointed, and/or flexible as may serve a particular implementation.

Tube 502 may include a plurality of channels 506 (e.g., a right-side imaging channel 506-R, a left-side imaging channel 506-L, and an illumination channel 506-I) configured to conduct light between the surgical area internal to the patient and camera head 504. Each channel 506 may include one or more optical fibers configured to carry light along tube 502 such that light generated within camera head 504 may be carried by illumination channel 506-I to be output at a distal end of tube 502 and, after reflecting from patient anatomy and/or other objects within the surgical area, carried by imaging channels 506-R and 506-L from the distal end of tube 502 back to camera head 504. Arrows shown within channels 506 in FIG. 5 are depicted to indicate the direction that light may travel within each channel. Additionally, it will be understood that tube 502 may be associated with (e.g., include) one or more lenses or other suitable optics (not explicitly shown) for focusing, diffusing, or otherwise treating light carried by channels 506 as may serve a particular implementation. In various other embodiments, there may be additional imaging and/or illumination channels. In still other embodiments, one or more image sensors and/or illuminators can be positioned closer to the distal end of tube 502, thereby minimizing or even eliminating the need for imaging and/or illumination channels through tube 502.

In some examples, stereoscopic endoscope 500 may be coupled to a robotic arm of a robotic surgical system (e.g., one of robotic arms 112 of robotic surgical system 100) and positioned such that a distal tip of tube 502 is disposed at a surgical area of a patient. In this configuration, stereoscopic endoscope 500 may be referred to as being located at or within the surgical area, even though a portion of stereoscopic endoscope 500 (e.g., camera head 504 and a proximal portion of tube 502) may be located outside the surgical area. While stereoscopic endoscope 500 is located at the surgical area, light reflected from the surgical area within a field of view of stereoscopic endoscope 500 may be captured by the distal tip of tube 502 and carried to camera head 504 by way of imaging channels 506-R and 506-L.

Camera head 504 may include various components configured to facilitate operation of stereoscopic endoscope 500. For example, as shown, camera head 504 may include image sensors 508 (e.g., an image sensor 508-R associated with right-side imaging channel 506-R and an image sensor 508-L associated with left-side imaging channel 506-L). Image sensors 508 may be implemented as any suitable image sensors such as charge coupled device ("CCD") image sensors, complementary metal-oxide semiconductor ("CMOS") image sensors, or the like. Additionally, one or more lenses or other optics may be associated with image sensors 508 (not explicitly shown). Camera head 504 may further include an illuminator 510 configured to generate light to travel from camera head 504 to the surgical area via imaging channel 506-I so as to illuminate the surgical area.

Camera head 504 may further include camera control units 512 disposed therein. Specifically, a camera control unit 512-R may be communicatively coupled to image sensor 508-R, and a camera control unit 512-L may be communicatively coupled to image sensor 508-L. Camera control units 512 may be synchronously coupled to one another by way of a communicative link 514, and may be implemented by software and/or hardware configured to control image sensors 508 so as to generate respective images 516 (i.e., an image 516-R associated with the right side and an image 516-L associated with the left side) based on light sensed by image sensors 508. As such, each respective combination of an imaging channel 506, an image sensor 508, a camera control unit 512, and associated optics may collectively be referred to as a camera included within stereoscopic endoscope 500. For example, stereoscopic endoscope 500 may include two such cameras, one for the left side and one for the right side. Such a camera may be said to capture an image 516 from a vantage point at a distal end of its respective imaging channel 506. Upon being generated by stereoscopic endoscope 500, images 516 may be accessed by a surgical instrument tracking system and/or otherwise used in any of the ways described herein. For example, images 516 may be used by a surgical instrument tracking system to determine positions of robotically-manipulated surgical instruments located at the surgical area in any of the ways described herein.

Figure 6:
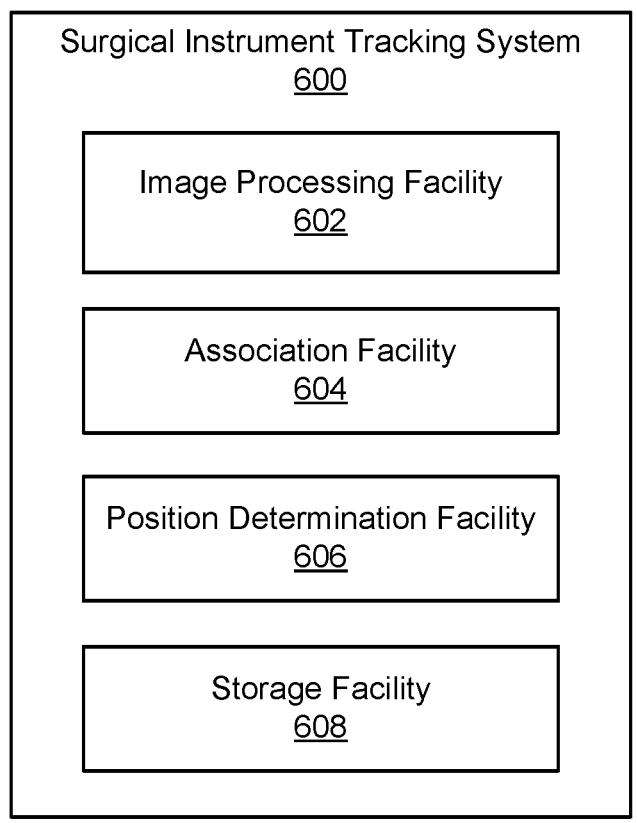
FIG. 6 illustrates an exemplary surgical instrument tracking system according to principles described herein.

FIG. 6 shows an exemplary surgical instrument tracking system 600 ("tracking system 600" or "system 600") configured to track surgical instruments located at a surgical area. As shown, system 600 may include, without limitation, an image processing facility 602, an association facility 604, a position determination facility 606, and a storage facility 608 selectively and communicatively coupled to one another. It will be recognized that although facilities 602 through 608 are shown to be separate facilities in FIG. 6, facilities 602 through 608 may be combined into fewer facilities, such as into a single facility, or divided into more facilities as may serve a particular implementation. Each of facilities 602 through 608 may be implemented by any suitable combination of computing hardware and/or software.

System 600 may be associated with a robotic surgical system such as robotic surgical system 100 in any suitable manner. For example, system 600 may be implemented by or included within a robotic surgical system. To illustrate, system 600 may be implemented by one or more computing devices included within patient-side system 102, surgeon console 104, and/or vision cart 106 of robotic surgical system 100. In some examples, system 600 may be at least partially implemented by one or more computing devices communicatively coupled to, but not included in, a robotic surgical system (e.g., one or more servers communicatively coupled to robotic surgical system 100 by way of a network).

Image processing facility 602 may be configured to access endoscopic imagery (sometimes referred to as "endoscopic images"), which may include a set of one or more images captured by or derived from images captured by an endoscope located at a surgical area associated with a patient. The set of one or more endoscopic images may include 2D images, 3D images, 3D images derived from 2D images, one or more pairs of temporally aligned stereoscopic images, frames of video, sequences of images, aggregate or combination images (e.g., an image formed by combining multiple images together), or images in any other suitable form. Endoscopic imagery may be represented as image data in any suitable data format (e.g., as data representing RGB images having any suitable number of image channels), which image data may be accessed by image processing facility 602.

In certain implementations, for example, image processing facility 602 may access a first image (e.g., image 516-L) captured from a first vantage point by a first camera included within a stereoscopic endoscope (e.g., stereoscopic endoscope 500) located at the surgical area and a second image (e.g., image 516-R) captured from a second vantage point stereoscopic to the first vantage point by a second camera included within the stereoscopic endoscope. Image processing facility 602 may access the images in any suitable manner. For example, image processing facility 602 may access the images by receiving them from an endoscope or by accessing them from storage facility 108 or other computer memory (e.g., a memory buffer).

While certain examples are described herein with reference to endoscopic imagery captured by an endoscope, in other examples, image processing facility 602 may process any suitable imagery of a surgical area. For example, image processing facility 602 may process surgical area imagery captured by one or more non-endoscopic cameras, multiple endoscopes, or a combination of at least one endoscope and at least one non-endoscopic camera.

Image processing facility 602 may process endoscopic imagery to determine observations for objects of interest depicted in the endoscopic imagery. The processing of the endoscopic imagery may include image processing facility 602 extracting features representing objects of interest from the endoscopic imagery. An "object of interest," as used herein, refers to any object or other feature depicted in endoscopic imagery and that is defined to be of interest to image processing facility 602. In certain examples, an object of interest may be represented by any feature depicted in endoscopic imagery that may be associated with a surgical instrument. For example, a feature may be a visual representation of a surgical instrument depicted in endoscopic imagery, a component of a surgical instrument depicted in endoscopic imagery, or any object depicted in endoscopic imagery that may be determined by image processing facility 602, correctly or incorrectly, to represent a surgical instrument or a component of a surgical instrument.

In certain implementations, an object of interest may be a marker-less component of a surgical instrument. A marker-less component of a surgical instrument may be a physical component of a surgical instrument that does not include a dedicated computer vision marker (e.g., a barcode, a color, etc.). By processing endoscopic imagery to extract marker-less objects of interest instead of dedicated computer vision markers, image processing facility 602 may overcome one or more problems associated with the use of dedicated computer vision markers, such as the costs to manufacture the markers, limited lifespans of the markers, inability to use the markers on all surgical instruments, occlusion of markers from camera view by anatomical tissue, blood, debris, or other instruments, and computing inefficiencies associated with conventional detection of the markers.

In certain implementations, an object of interest may be a distal clevis of a surgical instrument. A distal clevis of a surgical instrument may be the center of the most distal joint of a surgical instrument, and a position of the distal clevis may be used to determine a position of a distal tip of the surgical instrument. In some implementations, an extraction of the distal clevis of the surgical instrument from endoscopic imagery may be more accurate, easy, and/or reliable than an extraction of a small distal tip of the surgical instrument from endoscopic imagery. Additional or alternative components of surgical instruments (e.g., a shaft of a surgical instrument) may be defined to be objects of interest in other implementations.

Once image processing facility 602 has extracted an object of interest from endoscopic imagery, image processing facility 602 may define an observation for the object of interest. The observation may indicate a position of the object of interest that has been derived from the endoscopic imagery. Because the position is derived from the endoscopic imagery, the position may be referred to as an "image-based position." In certain examples, the observation may be defined to represent the position as a 2D region in a 2D space or a 3D region in a 3D space. For example, the observation may indicate a defined pixel area region on a projected 2D image plane (e.g., projected from the vantage point of an endoscopic camera). As another example, the observation may indicate a defined 3D region such as a 3D region within a 3D space defined by a world 3D coordinate system associated with robotic surgical system 100.

In certain examples, in addition to representing a position of an object of interest, an observation defined by image processing facility 602 (e.g., as output of a neural network) may indicate one or more other attributes of the object of interest. For example, an observation may indicate a motion cue (e.g., a velocity, an acceleration, etc.) associated with the object of interest (which may be derived from a sequence of images such as a sequence of video frames), a type of surgical instrument associated with the object of interest (e.g., that the object of interest is attached to a needle driver, grasper, or cautery type of surgical tool), an additional position associated with the object of interest (e.g., a position of another component of the object of interest), a position of another object of interest relative to the position of the object of interest (e.g., a position of a surgical instrument tip, shaft, etc. relative to a distal clevis of the surgical instrument), and/or an orientation associated with the object of interest (e.g., an orientation of a distal clevis).

Image processing facility 602 may be configured to use a trained neural network to determine an observation for an object of interest. For example, image processing facility 602 may use a convolutional neural network ("CNN") or another deep, feed-forward artificial neural network to extract an object of interest and define an observation for the object of interest.

To this end, a neural network may be trained such that the neural network is configured to determine an observation for an object of interest depicted in endoscopic imagery. The training may be performed in any suitable way, such as by using labeled (e.g., hand-labeled) data as a training set. Such data may include endoscopic imagery that has been labeled with observations of any objects of interest depicted in the endoscopic imagery. For example, training imagery may include an image that depicts an object of interest and a label indicating an image-based position associated with the object of interest. The label may be in any suitable form, such as a bounding box defining a rectangular area (e.g., a pixel region) positionally associated with an object of interest, or any other suitable definition of an area of an image that is positionally associated with the object of interest.

Other images in the training imagery may be similarly labeled to indicate positions associated with objects of interest. Yet other images in the training imagery may be labeled (or not labeled) to indicate that no object of interest is depicted in the images. In some examples, additional labels may be added to the training imagery to indicate other properties of objects of interest, such as labels indicating types of surgical instruments and/or additional components of surgical instruments. Examples of other labels that may be used include, but are not limited to, labels indicating key points on surgical instruments (e.g., instrument tips, features on instrument surfaces such as logos or other indicia on instrument surfaces, instrument shaft, instrument shaft axis, etc.) and labels indicating per-pixel segmentations of the instrument or components of the instrument (e.g., the instrument body or parts of the instrument body). Certain images in the training imagery may be selected for use in training the neural network based on discrepancies between the content of the images and corresponding kinematics for surgical instruments, such as an image that does not depict a surgical instrument when corresponding kinematics indicate that the surgical instrument should be within view of an endoscope that captured the image.

After the neural network has been trained, image processing facility 602 may use the trained neural network to determine an observation for an object of interest depicted in endoscopic imagery. In certain examples, image processing facility 602 may do this by providing endoscopic imagery as input to the trained neural network, which may process the endoscopic imagery and output a determined observation for an object of interest depicted in the imagery and extracted by the trained neural network. The trained neural network may determine the observation for the object of interest by selecting, from observations that were previously generated (e.g., labeled during training of the neural network) for historical and/or training endoscopic imagery, the observation that is the best or most likely match to the endoscopic imagery being processed. In other examples, instead of outputting an observation for an object of interest, the trained neural network may output data indicative of an extracted object of interest, and image processing facility 602 may use this output from the trained neural network to define or supplement the observation for the object of interest, such as by defining an area that encompasses the object of interest and/or adding another property to the observation. Examples of image processing facility 602 determining observations for objects of interest depicted in endoscopic imagery are described herein.

An observation determined by image processing facility 602 for an object of interest may be considered to indicate a candidate, image-based position for a surgical instrument at least because image processing facility 602 has not associated the observation determined and output by image processing facility 602 with any particular surgical instrument at the surgical area. Image processing facility 602 may provide data representative of the observation for access and use by association facility 604 to associate the observation to an appropriate surgical instrument that is determined by association facility 604 to be represented by the object of interest, or to a false positive designation when association facility 604 determines that the object of interest does not represent a surgical instrument at the surgical area.

Association facility 604 may access data representative of an observation for an object of interest from image processing facility 602 and associate, based on kinematics of one or more surgical instruments at the surgical area, the observation for the object of interest to a particular surgical instrument or to a false positive designation. In certain implementations, association facility 604 may be configured to determine an association to be made based on a probabilistic framework and kinematics of one or more surgical instruments at the surgical area. As an example, association facility 604 may determine, based on kinematics of one or more surgical instruments at the surgical area, a probability for a potential association of an observation for an object of interest to each surgical instrument at the surgical area and to a false positive designation. Association facility 604 may then select the highest probability association and associate the observation to the surgical instrument or the false positive designation having the highest probability. As another example, association facility 604 may determine, based on kinematics of one or more surgical instruments at the surgical area, a probability for each possible set of one-to-one associations between observations and surgical instruments or false positive designations. Association facility 604 may then select the highest probability set of one-to-one associations and associate the observations to the respective surgical instruments or false positive designations in accordance with the selected set of associations. Examples of association facility 604 using a probabilistic framework and kinematics to associate observations to surgical instruments or false positive designations are described herein.

Association facility 604 may output data representative of associations made by association facility 604, such as data representing an observation and an associated surgical instrument. In some examples, association facility 604 may refrain from outputting data representative of an observation that is associated with a false positive designation.

Position determination facility 606 may access data output by association facility 604, such as data representing an observation and an associated surgical instrument. Position determination facility 606 may use the accessed data to determine a physical position of the surgical instrument at the surgical area based on kinematics of the surgical instrument and the observation associated with the surgical instrument.

In certain examples, position determination facility 606 may implement and use a non-linear estimator such as an unscented Kalman filter or other Bayesian filter to determine a physical position of a surgical instrument at a surgical area based on kinematics of the surgical instrument and an observation associated with the surgical instrument. For example, position determination facility 606 may input the observation and the kinematics into an unscented Kalman filter, which may use the observation and the kinematics to determine and output a physical position of the surgical instrument at the surgical area. The physical position of the surgical instrument at the surgical area may be represented in any suitable way, including as coordinates representing a 3D position of a component of the surgical instrument (e.g., a 3D position of a distal clevis or a distal tip of the surgical instrument) in a 3D space such as a world 3D space associated with robotic surgical system 100.

In certain implementations, position determination facility 606 may be configured to determine a physical position of a surgical instrument by correcting a kinematic-based position of the surgical instrument represented by the kinematics, based on an image-based position of the object of interest represented by the observation. For example, an unscented Kalman filter may be configured to adjust the kinematic-based position of the surgical instrument based on the image-based position of the object of interest indicated by the observation. The adjustment may be made in any suitable way, such as by applying a corrective transform to the kinematic-based position. In certain implementations, position determination facility 606 may be configured to apply the corrective transform to the kinematic-based position as fast as possible, which may be as fast as image processing facility 602 is able to extract objects of interest from endoscopic imagery and determine observations for relevant objects of interest. By correcting kinematic-based positions with observed image-based positions, tracking system 600 is able to use kinematics when observations are unavailable, such as when a surgical instrument is not extractable from endoscopic imagery (e.g., when the surgical instrument is hidden behind tissue, when there is a lot of smoke in the surgical area, when the surgical instrument is outside the field of view of an endoscope, etc.). When an observation for an object of interest representative of the surgical instrument is available and used to correct a kinematic-based position of the surgical instrument, tracking system 600 is able to track the physical position of the surgical instrument with more precision and/or accuracy than when kinematics are used alone without an observation. This may be helpful to remove or reduce errors in kinematic-based positions (e.g., an error in an instrument tip position caused by an accumulation of errors in joint encoders along a robotic system kinematic chain), such as rigid errors that may be found when determining absolute position in global 3D world coordinates based on kinematics alone and/or errors that may be introduced by large movements of the surgical instrument (which may be mounted on a long kinematic chain).

A physical position of a surgical instrument determined by position determination facility 606 may be used to track the surgical instrument at a surgical area during a surgical session. By tracking the surgical instrument in this manner, robotic surgical system 100 may provide one or more features that utilize the tracked physical position of the surgical instrument. Examples of such features are described herein.

Storage facility 608 may store and maintain any data received, generated, managed, maintained, used, and/or transmitted by facilities 602 through 606 in a particular implementation. For example, storage facility 608 may store program instructions (e.g., computer code) for performing operations described herein, image data, observation data, kinematic data, position data, and/or any other data as may serve a particular implementation.

Figure 7:
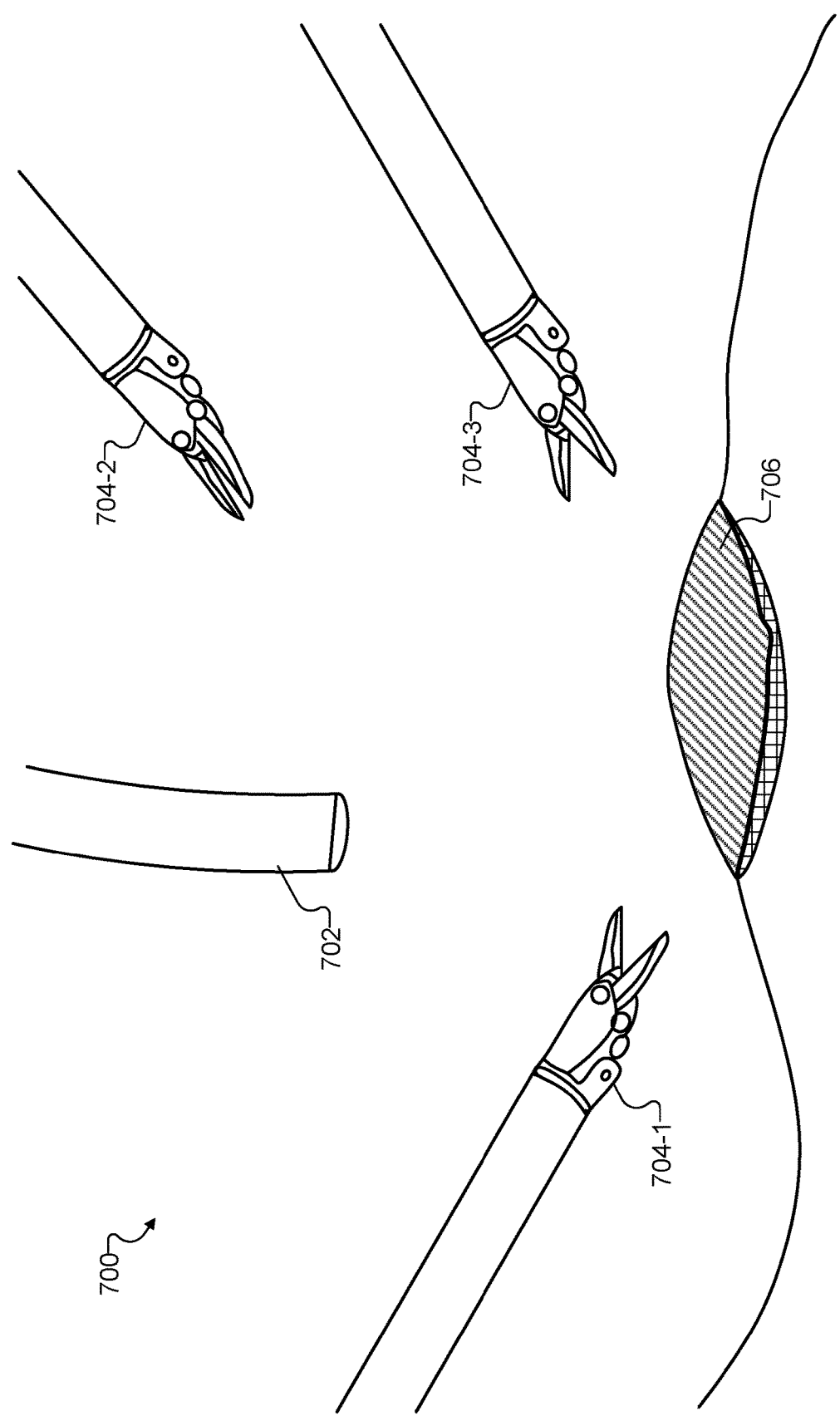
FIG. 7 illustrates a view of surgical instruments within a surgical area according to principles described herein.

An example of system 600 tracking a surgical instrument by determining a physical position of the surgical instrument will now be described with reference to FIGS. 7-10. FIG. 7 illustrates a view 700 of surgical instruments within a surgical area. As shown, the surgical instruments may include an endoscope 702 and one or more other surgical instruments 704 (e.g., surgical instruments 704-1 through 704-3) in the form of one or more surgical tools. While FIG. 7 shows one endoscope 702 and three surgical tools located at the surgical area, any number and/or combination of endoscopes and surgical tools may be at the surgical area during a surgical session. Tissue 706 represents anatomical tissue at the surgical area.

Endoscope 702 may capture endoscopic imagery at the surgical area. Any of surgical instruments 704 and/or tissue 706 that are within a field of view of endoscope 702 may be depicted in the endoscopic imagery captured by endoscope 702.

Figure 8:
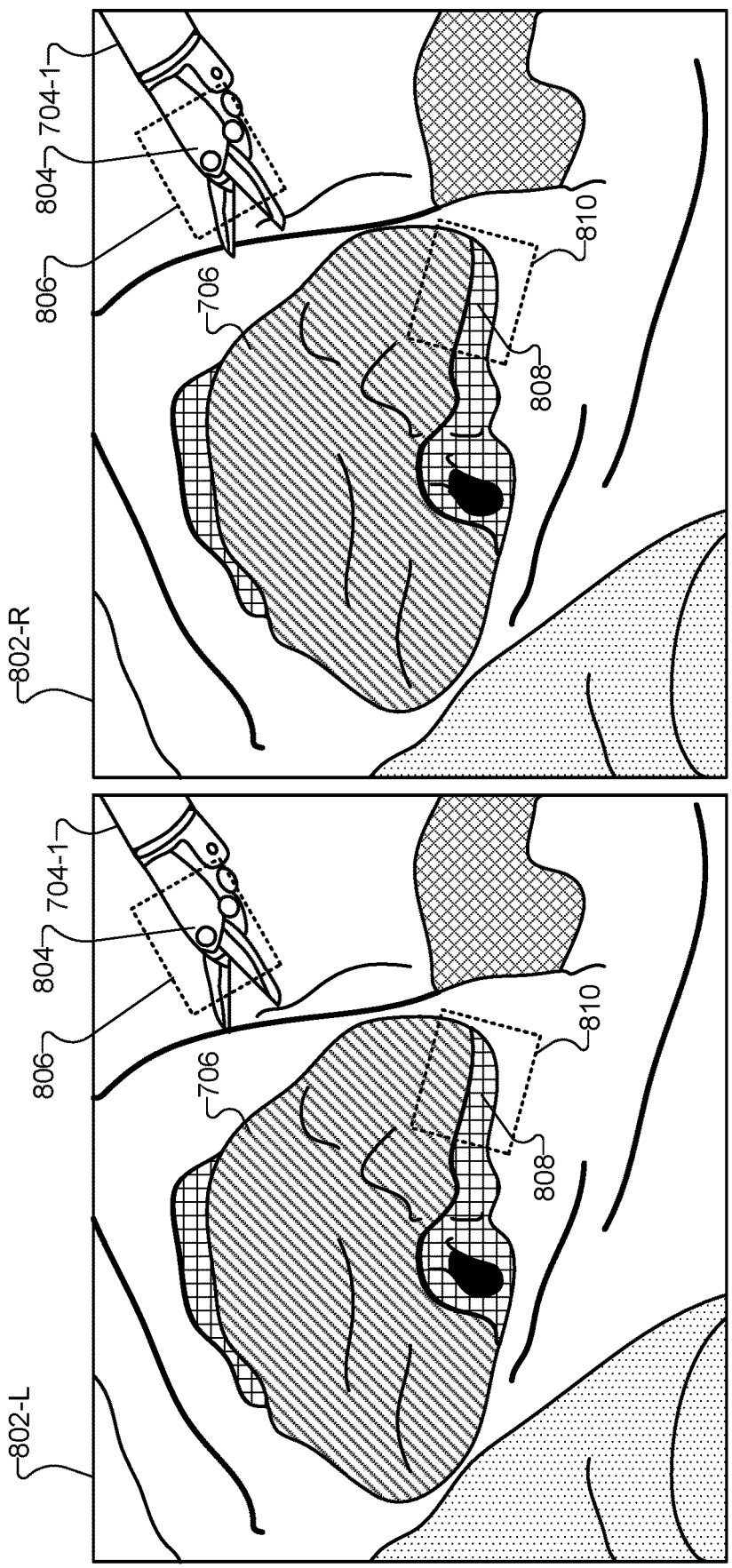
FIG. 8 illustrates exemplary endoscopic images of a surgical area according to principles described herein.

FIG. 8 illustrates exemplary images 802 (i.e., images 802-L and 802-R) of a surgical area as captured from stereoscopic vantage points by cameras included within endoscope 702, which in this example is a stereoscopic endoscope. Images 802-L and 802-R may respectively implement images 516-L and 516-R described above. As shown, each image 802 depicts a portion of tissue 706 and surgical instrument 704-1 that are within the field of view of endoscope 702.

As illustrated, images 802 are relatively similar one to another. However, it will be understood that slight differences also exist between images 802 due to the stereoscopic nature of the vantage points from which each image 802 is captured. As such, images 802 may appear to be three-dimensional when image 802-L is presented to a left eye of a user (e.g., surgeon 110-1) while image 802-R is presented to a right eye of the user.

As with images 516, either or both of images 802 may be displayed or presented by system 600 in any suitable way and/or on any suitable display screen. For example, one or both of images 802 may be displayed on display monitor 122 of vision cart 106, on stereo viewer 402 on surgeon console 104, on a monoscopic display provided by endoscope 702, and/or on any other display screen associated with robotic surgical system 100 or tracking system 600.

Image processing facility 602 may process one or both of images 802 to determine an observation for any object of interest depicted in images 802. For example, image processing facility 602 may provide images 802 as input to a trained neural network, which may extract, from images 802, any object of interest depicted in images 802. For instance, using the trained neural network, image processing facility 602 may extract an object of interest 804 that represents a distal clevis of surgical instrument 704-1 in each of images 802. Image processing facility 602 may then define, based on images 802 and the extracted object of interest 804, an observation for the object of interest 804. For example, image processing facility 602 may define an observation that includes a bounding box 806 representing an image-based position of the distal clevis in each of images 802. While a rectangular bounding box 806 is illustrated in FIG. 8 to represent an image-based position indicated by an observation for object of interest 804, any suitable geometric region (e.g., an ellipse), coordinate point (s), or other position indicator may be used in other examples to represent an image-based position indicated by an observation for an object of interest. For example, bounding boxes or other position indicators may be defined to identify any instrument part (e.g., an instrument tip, shaft, indicia, etc.) In certain other examples, an observation may define lines forming an instrument "skeleton," or an observation may define per-pixel segmentations of instruments or parts of instruments (e.g., an image in which pixels representing an instrument part and pixels not representing the instrument part are represented as different binary values such as black and white color values). Also, while a distal clevis is represented by object of interest 804 in each of images 802, any suitable object of interest, such as an additional or alternative component of a surgical instrument may be defined to be an object of interest that is extractable by a trained neural network.

In certain examples, image processing facility 602, using the trained neural network, may extract an object of interest based on features that indicate that the object of interest may represent a surgical instrument, even though the object of interest is not actually representative of a surgical instrument. For instance, using the trained neural network, image processing facility 602 may extract an object of interest 808 that is actually a portion of tissue 706 that has features that indicate that the object of interest 808 may represent a surgical instrument. Image processing facility 602 may then define, based on images 802 and the extracted object of interest 808, an observation for the object of interest 808. As shown in FIG. 8, for example, image processing facility 602 may define an observation that includes a bounding box 810 representing an image-based position of object of interest 808 in each of images 802.

Image processing facility 602 may similarly extract any other object of interest depicted in images 802 (e.g., an object of interest representative of another surgical instrument if another surgical instrument is within the field of view of endoscope 702) and define an observation for that object of interest.

An observation determined by image processing facility 602 for an object of interest may represent an image-based position of the object of interest in any suitable way. For example, the observation may represent a 2D area within an image (e.g., a pixel region or other 2D area on a projection plane projected from a viewpoint such as the viewpoint of endoscope 702). As another example, the observation may represent a 3D region within a 3D space represented by a world 3D coordinate system, which 3D region may be derived from identified 2D areas within endoscopic imagery (e.g., from 2D areas in stereoscopic endoscopic images). As another example, the observation may be a single coordinate location or a set of one or more coordinate locations in a 2D area or a 3D space. Examples of such observations are described in more detail herein.

In certain examples, image processing facility 602 may have no information of surgical instruments 704 or kinematics of surgical instruments 704 and may determine an observation based exclusively on endoscopic imagery and using a trained neural network (e.g., by inputting the endoscopic imagery to the trained neural network, which outputs the observation). Thus, image processing facility 602 may not determine whether the observation represents a surgical instrument or a false positive designation, or which specific surgical instrument is represented by the observation.

Association facility 604 may associate each determined observation to a particular one of surgical instruments 704 or a false positive designation based on a probabilistic framework and kinematics of one or more of surgical instruments at the surgical area (e.g., kinematics of endoscope 702 and/or one or more of surgical instruments 704). In certain implementations, this may include association facility 604 determining, for an observation determined by image processing facility 602, a probability of each potential association and selecting the potential association having the highest probability.

As an example, association facility 604 may determine, based on one or more suitable probability algorithms that take into account kinematics (e.g., 3D kinematic-based positions indicated by the kinematics) of one or more surgical instruments at the surgical area, a probability that bounding box 806 represents surgical instrument 704-1, a probability that bounding box 806 represents surgical instrument 704-2, a probability that bounding box 806 represents surgical instrument 704-3, and a probability that bounding box 806 represents a false positive. Association facility 604 may then select the highest determined probability and associate bounding box 806 to the surgical instrument 704 or false positive having the highest probability. For the scenario illustrated in FIG. 8, association facility 604 may determine that an association of bounding box 806 with surgical instrument 704-1 has the highest probability based at least in part on a proximate distance relationship between the kinematic-based position of surgical instrument 704-1 (as indicated by the kinematics) and an image-based position of the observation represented by bounding box 806 (e.g., compared to more distant relationships between the image-based position of the observation represented by bounding box 806 and kinematic-based positions of surgical instruments 704-2 and 704-3).

Figure 9:
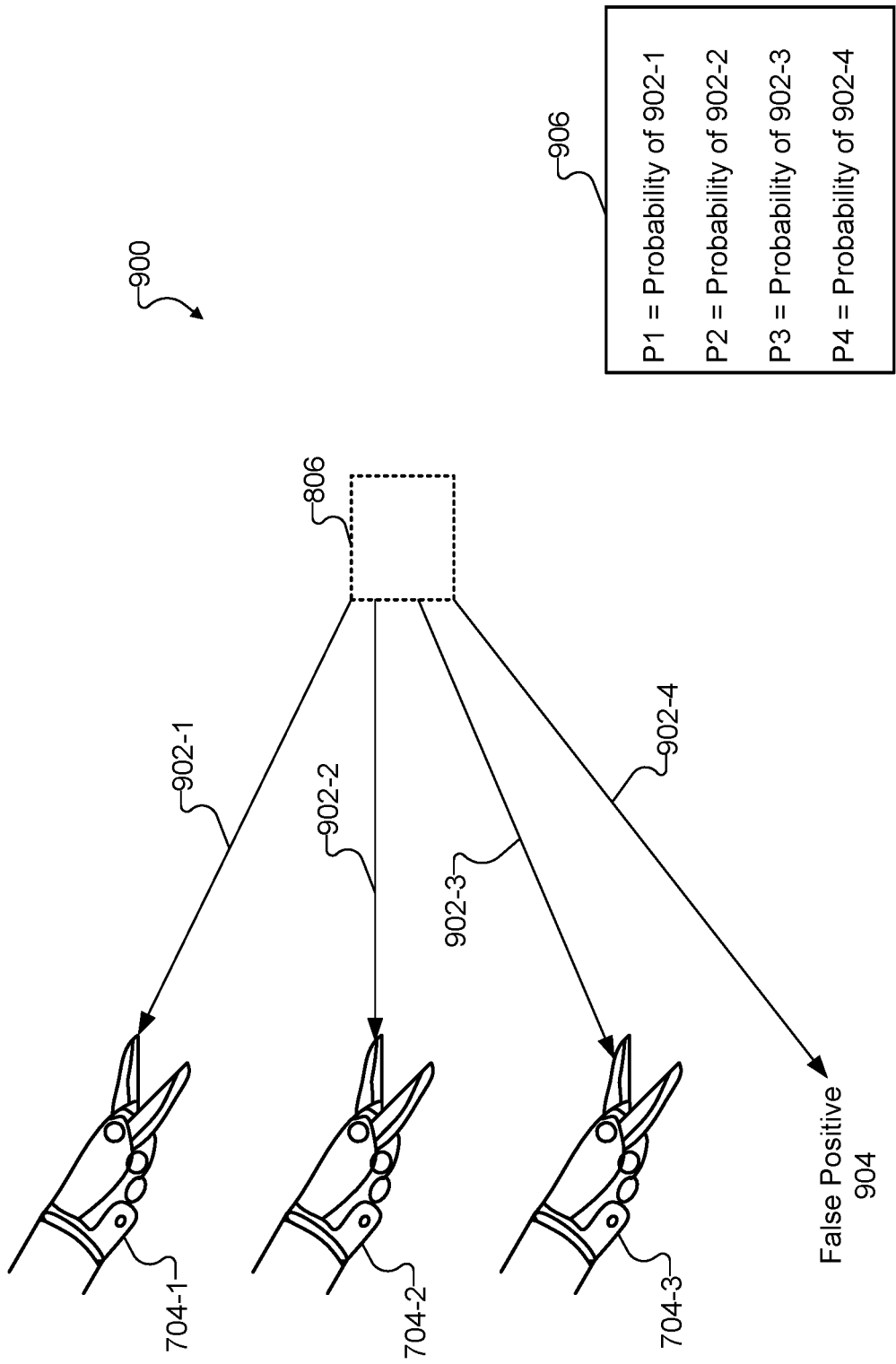
FIGS. 9-10 illustrate exemplary probabilistic frameworks according to principles described herein.

FIG. 9 illustrates an exemplary probabilistic framework 900 that may be used by association facility 604 to associate bounding box 806 with surgical instrument 704-1 in the above-described example. In the illustrated probabilistic framework 900, association facility 604 determines a probability P1 for a potential association 902-1 of bounding box 806 with surgical instrument 704-1, a probability P2 for a potential association 902-2 of bounding box 806 with surgical instrument 704-2, a probability P3 for a potential association 902-3 of bounding box 806 with surgical instrument 704-3, and a probability P4 for a potential association 902-1 of bounding box 806 with a false position designation 904. In FIG. 9, box 906 contains determined probabilities P1, P2, P3, and P4 for the respective potential associations. Association facility 604 may select the highest probability value from P1, P2, P3, and P4 and define an association of bounding box 806 to a particular surgical instrument 704 or false positive designation 904 in accordance with the potential association having the highest probability.

As another example of using such a probabilistic framework, association facility 604 may determine, based on one or more suitable probability algorithms that take into account kinematics of one or more surgical instruments at the surgical area, a probability that bounding box 810 represents surgical instrument 704-1, a probability that bounding box 810 represents surgical instrument 704-2, a probability that bounding box 810 represents surgical instrument 704-3, and a probability that bounding box 810 represents a false positive. Association facility 604 may then select the highest determined probability and associate bounding box 810 to the surgical instrument 704 or false positive having the highest probability. For the scenario illustrated in FIG. 8, association facility 604 may determine that an association of bounding box 810 with a false positive designation has the highest probability based at least in part on a lack of a proximate distance relationship between an image-based position of the observation represented by bounding box 810 and kinematic-based positions of surgical instruments 704.

In certain implementations, association facility 604 may determine and make a highest-probability-based association individually for each observation determined by image processing facility 602, such as in the examples described above. In making such an association for an observation, association facility 604 may determine probabilities of potential associations of the observation without regard to other observations determined from endoscopic imagery. Thus, an association of an observation to a surgical instrument or a false positive designation may be made independent of associations of any other observations determined from endoscopic imagery. For example, an observation represented by bounding box 806 may be associated with a surgical instrument 704 or a false positive designation independently of an observation represented by bounding box 810 and/or independently of an association of the observation represented by bounding box 810 to a surgical instrument or a false positive designation.

In other implementations, when determining a highest-probability-based association of an observation, association facility 604 may account for one or more other observations and/or associations of the observations. Such other observations may include an observation determined from the same endoscopic imagery (e.g., from the same endoscopic image), an observation determined from another endoscopic image such as a stereoscopic image, and/or an observation determined from older-in-time endoscopic imagery such as a previous video frame.

In certain implementations, association facility 604 may be configured to determine and make highest-probability-based associations by collectively considering all observations determined by image processing facility 602 from endoscopic imagery. For example, as part of determining probabilities of potential associations of an observation determined by image processing facility 602 from endoscopic imagery, association facility 604 may determine and consider probabilities of potential associations of one or more other observations determined by image processing facility 602 from the endoscopic imagery. Association facility 604 may consider the probabilities collectively to determine highest-probability associations of the observations.

In certain examples, association facility 604 may collectively determine probabilities of potential associations by determining a probability for each potential set of associations between observations and surgical instruments or false positives. For the scenario illustrated in FIG. 8, for example, association facility 604 may determine a probability for each potential set of associations of bounding boxes 806 and 810 to surgical instruments 704 or false positives and select the set of associations that has the highest probability. For example, association facility 604 may determine that a set of associations in which bounding box 806 is associated with surgical instrument 704-1 and bounding box 810 is associated with a false positive designation has a higher probability (as a set) than each other potential set of associations.

Figure 10:
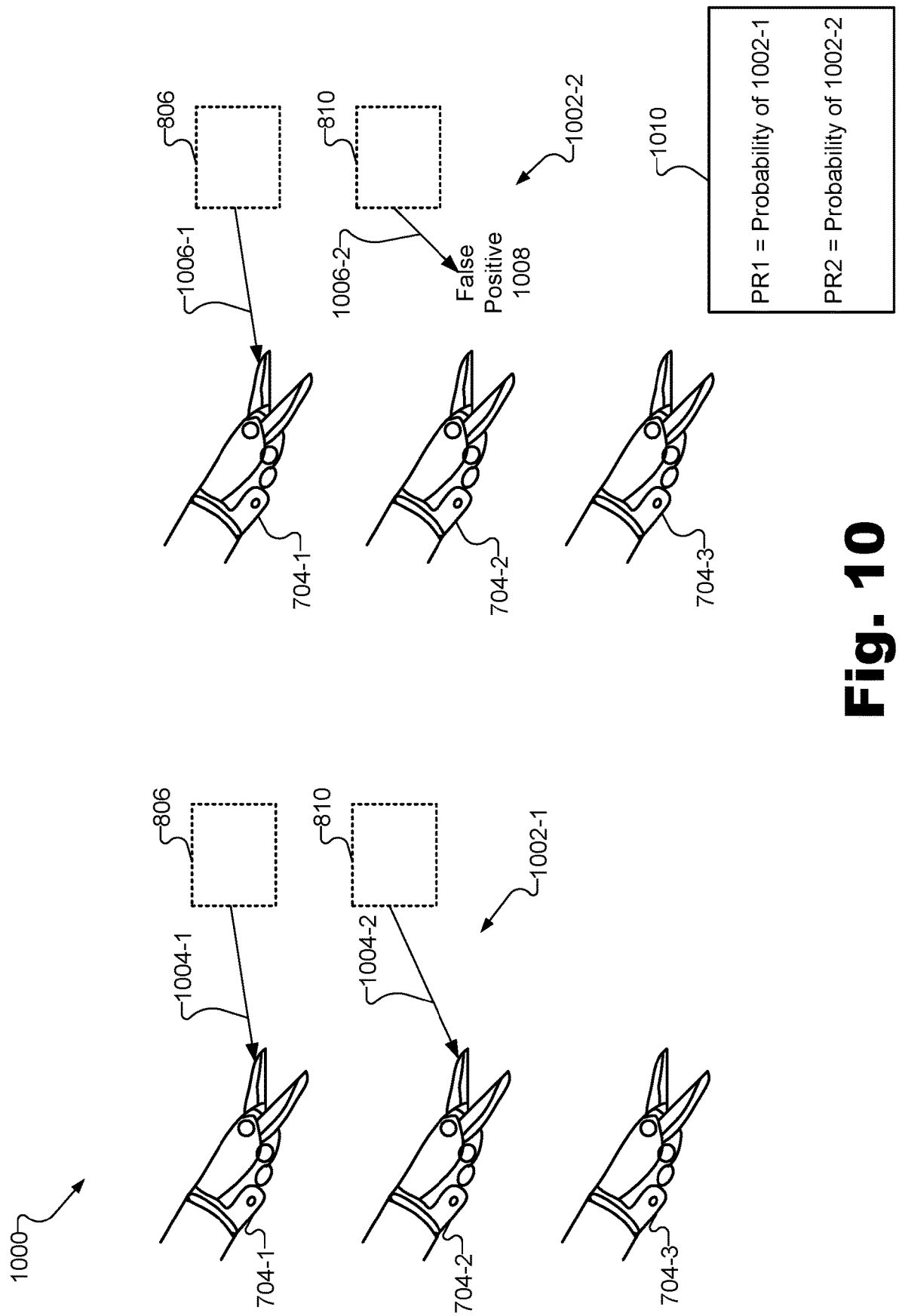

FIG. 10 illustrates an exemplary probabilistic framework 1000 that may be used to associate bounding box 806 with surgical instrument 704-1 and bounding box 810 with a false positive designation in the above-described example. Based on the illustrated probabilistic framework 1000, association facility 604 may determine a probability PR1 for a first set 1002-1 of potential associations and a probability PR2 for a second set 1002-2 of potential associations. As shown, the first set 1002-1 of potential associations includes a potential association 1004-1 of bounding box 806 to surgical instrument 704-1 and a potential association 1004-2 of bounding box 810 to surgical instrument 704-2. The first set 1002-1 of potential associations includes no potential associations to surgical instrument 704-3 or to a false positive designation. As also shown, the second set 1002-2 of potential associations includes a potential association 1006-1 of bounding box 806 to surgical instrument 704-1 and a potential association 1006-2 of bounding box 810 to a false positive designation 1008. The second set 1002-2 of potential associations includes no potential associations to surgical instruments 704-2 and 704-3. The first set 1002-1 and the second set 1002-2 of potential associations represent two possible sets of potential one-to-one associations between bounding boxes 806 and 810 and surgical instruments 704-1, 704-2, and 704-3 or false positive designations. Association facility 604 may determine a probability for each possible set of potential associations, including for the first set 1002-1 and the second set 1002-2 of potential associations.

In FIG. 10, for illustrative purposes box 1010 contains only the determined probabilities PR1 and PR2 for the respective sets 1002-1 and 1002-2 of potential associations. Association facility 604 may select the highest probability value from PR1 and PR2 (and probabilities for any other set(s) of potential associations) and define associations of bounding box 806 and bounding box 810 to a respective surgical instrument 704 or false positive designation 1008 in accordance with the set of potential associations having the highest probability. For example, association facility 604 may select the second set 1002-2 of potential associations as having the highest probability based on the probabilistic framework and the kinematics of one or more surgical instruments 704-1, 704-2, and 704-3 and may associate bounding box 806 to surgical instrument 704-1 and bounding box 810 to a false positive designation 1008 in accordance with the second set 1002-2 of potential associations.

The above-described examples of probabilistic frameworks are illustrative only. Association facility 604 may implement any suitable probability algorithms and/or probabilistic framework to determine probabilities of potential associations and/or sets of potential associations. The probability algorithms may be configured to account for kinematic-based positions of one or more surgical instruments in probability determinations. In certain implementations, the probability of each potential association or each set of potential associations may be conditionally independent given the potential associations or sets of potential associations, and appropriate probability algorithms for such conditional independence may be used as a probabilistic framework by association facility 604.

Association facility 604 may use any suitable kinematic information to determine probabilities of potential associations of observations to surgical instruments or false positives. In certain embodiments, for example, association facility 604 may use kinematics and/or other properties of endoscope 702 (e.g., orientation, field of view, lens properties, etc.) to determine probabilities of potential associations. For example, association facility 604 may use a kinematic-based position and an orientation of endoscope 702 and a kinematic-based position and/or orientation of a surgical instrument 704 (e.g., a position and/or orientation of a specific instrument part such as an instrument shaft, tip, clevis, etc.) to determine a probability that the surgical instrument 704 is within the field of view of endoscope 702, which probability may be used by association facility 604 to determine a probability that bounding box 806 corresponds to the surgical instrument 704 or a false positive and/or a probability that bounding box 810 corresponds to the surgical instrument 704 or a false positive.

Association facility 604 may be configured to use any suitable information about surgical instruments to determine probabilities of potential associations of observations to surgical instruments or false positives. For example, association facility 604 may use information about a type of surgical instrument indicated by kinematic information, information about an observed type of surgical instrument indicated by an observation, and/or information about position and/or orientation of surgical instruments parts (e.g., a shaft, tip, clevis, etc. of a surgical instrument) indicated by kinematic information and/or the observation.

A probabilistic framework used by association facility 604 may include an observation model that defines a conditional probability function to be used by association facility 604 to determine a probability that an observation represents a surgical instrument or a false positive based on a current state of a robotic surgical system (e.g., based on kinematics of a surgical instrument and/or any other state information for the robotic surgical system).

In certain alternative implementations, association facility 604 may be configured to associate an observation to a surgical instrument or a false positive designation based on kinematics of surgical instruments at the surgical area and without using a probabilistic framework. For example, association facility 604 may be configured to associate an observation to a most proximate surgical instrument that is within a predefined distance threshold or to a false positive designation when no surgical instrument is within the predefined distance threshold.

Association facility 604 may define or otherwise establish an association in any suitable way, such as by associating data representative of an observation to data representative of a corresponding surgical instrument or false positive designation. Association facility 604 may output data representative of a determined association between an observation and a surgical instrument. In some examples, association facility 604 may refrain from outputting data representative of a determined association between an observation and a false positive designation such that position determination facility 606 accesses and uses only observations that association facility 604 has associated with surgical instruments located at a surgical area.

Position determination facility 606 may be configured to access and use data representative of an observation and an associated surgical instrument to determine a physical position of the surgical instrument at the surgical area, based on the observation and kinematics for the associated surgical instrument. For example, position determination facility 606 may determine a physical position of surgical instrument 704-1 at the surgical area, based on bounding box 806 and kinematics for surgical instrument 704-1. Because association facility 604 has defined an association between the observation and the surgical instrument, position determination facility 606 is able to select and use, in combination with the observation, kinematics for the appropriate corresponding surgical instrument for the observation, to determine a physical position of the surgical instrument.

In certain examples, position determination facility 606 may implement a non-linear estimator, such as an unscented Kalman filter, a particle filter, or other Bayesian filter, to determine the physical position of a surgical instrument based on kinematics of the surgical instrument and one or more observations associated with the surgical instrument. Position determination facility 606 may do this by providing the kinematics and the one or more observations for the surgical instrument as input to the non-linear estimator, which may process the inputs and generate and output a determined physical position of the surgical instrument.

A physical position of a surgical instrument, as determined by position determination facility 606, may represent any suitable part of the surgical instrument (e.g., a distal clevis or an instrument tip of the surgical instrument). In certain examples, the physical position of the surgical instrument, as determined by position determination facility 606, may indicate a 3D position within world 3D space for a robotic surgical system such as robotic surgical system 100. The physical position may be represented in any suitable way and/or using any suitable data format.

FIGS. 11-14 illustrate exemplary implementations of tracking system 600 that include a trained neural network, a probabilistic framework, and a filter. In such implementations, image processing facility 602 may implement the trained neural network, association facility 604 may implement the probabilistic framework, and position determination facility 606 may implement the filter, which may be an unscented Kalman filter or other Bayesian filter. The implementations shown in FIGS. 11-14 may be configured to use various forms of endoscopic imagery and observations to determine physical positions of surgical instruments.

Accordingly, FIGS. 11-14 illustrate data flows associated with the exemplary implementations of tracking system 600.

Figure 11:
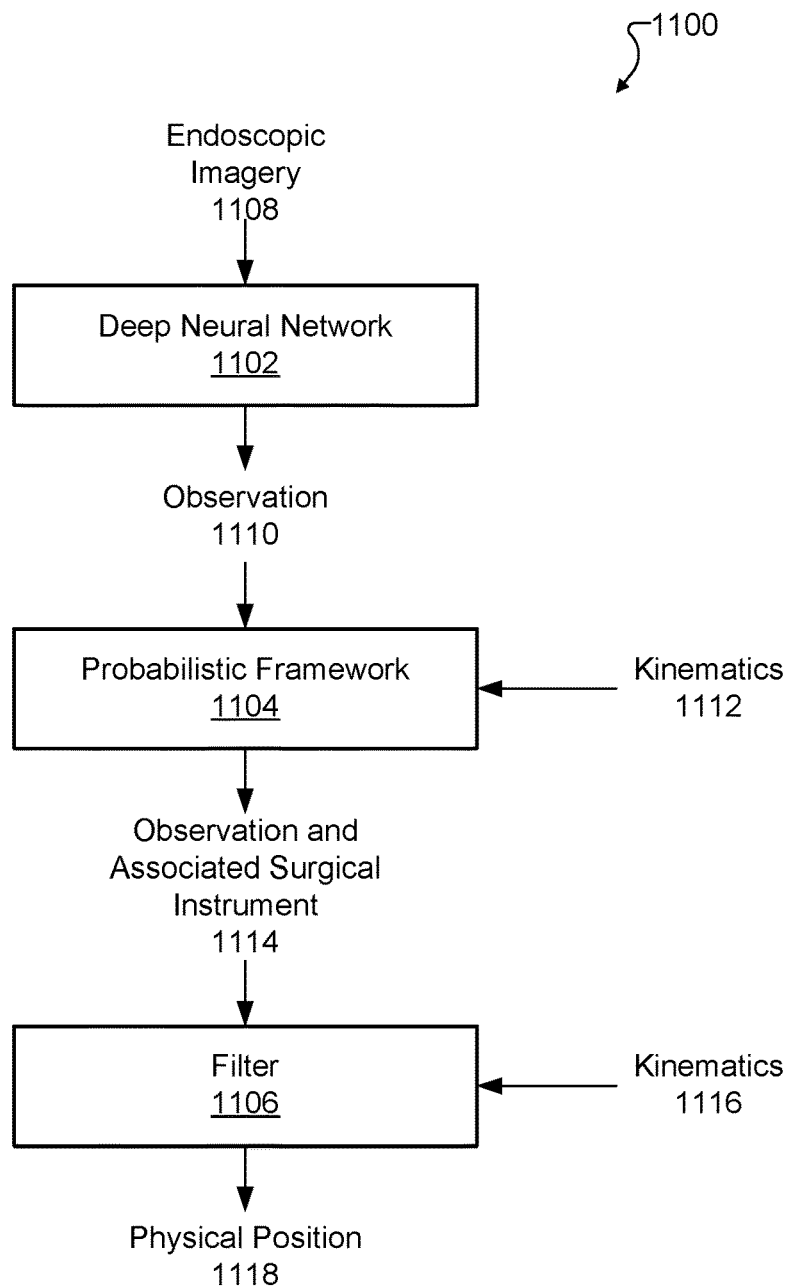
FIGS. 11-14 illustrate exemplary implementations of a surgical instrument tracking system according to principles described herein.

FIG. 11 illustrates an exemplary implementation 1100 that includes a trained neural network 1102, a probabilistic framework 1104, and a filter 1106. As shown, endoscopic imagery 1108 of a surgical area may be input to neural network 1102, which may determine, based on endoscopic imagery 1108, an observation 1110 in any of the ways described herein. Observation 1110 and kinematics 1112 of one or more surgical instruments may then be input to probabilistic framework 1104, which may be used to associate observation 1110 to a particular surgical instrument or a false positive designation based on kinematics 1112. For example, association facility 604 may determine, based on kinematics 1112 and using probabilistic framework 1104, probabilities of potential associations for observation 1110 and select the association with the highest probability.

When observation 1110 is associated with a particular surgical instrument using probabilistic framework 1104, data 1114 representative of observation 1110 and the associated surgical instrument may be output for use as input to filter 1106. Filter 1106 may receive and use kinematics 1116 for the associated surgical instrument and the data 1114 representative of the observation 1110 associated with the surgical instrument to determine and output a physical position 1118 of the surgical instrument at the surgical area.

Figure 12:
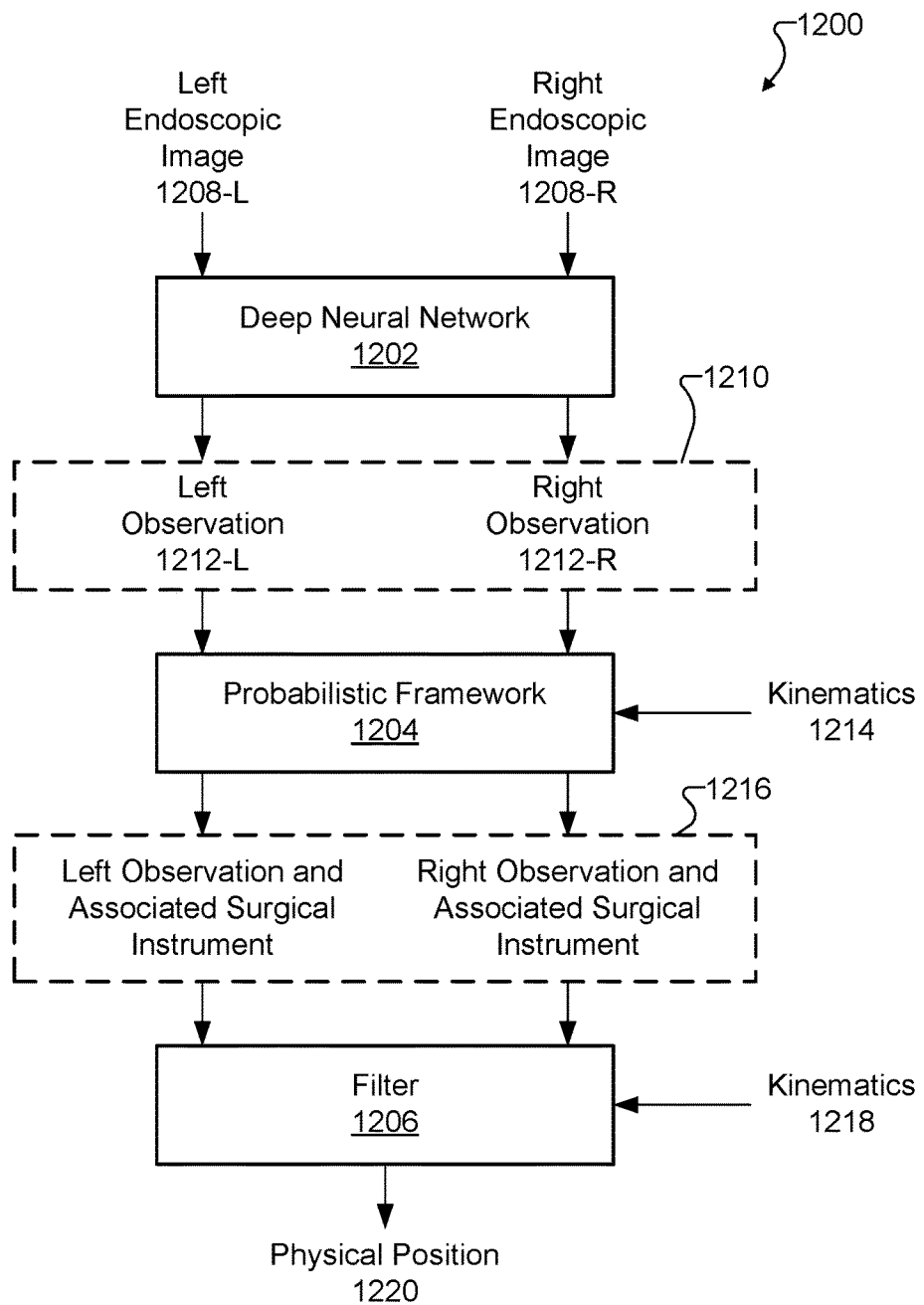

FIG. 12 illustrates an exemplary implementation 1200 that includes a trained neural network 1202, a probabilistic framework 1204, and a filter 1206. In the illustrated example, endoscopic imagery may include endoscopic images 1208, e.g., a left endoscopic image 1208-L and a right endoscopic image 1208-R (which may be a pair of 2D images that are stereoscopic to one another), that may be input to neural network 1202. Neural network 1202 may determine, based on endoscopic images 1208, an observation 1210 in any of the ways described herein. As shown, observation 1210 may include a left observation 1212-L and a right observation 1212-R (collectively referred to as "observations 1212"). Neural network 1202 may determine left observation 1212-L based on left endoscopic image 1208-L, and right observation 1212-R based on right endoscopic image 1208-R. Neural network 1202 may be configured to process left endoscopic image 1208-L and right endoscopic image 1208-R individually, one at a time, or in parallel to determine left observation 1212-L and right observation 1212-R.

Observations 1212 and kinematics 1214 of one or more surgical instruments may be input to probabilistic framework 1204, which may be used to associate each of the observations 1212 to a particular surgical instrument or a false positive designation based on kinematics 1214. For example, association facility 604 may determine, based on kinematics 1214 and using probabilistic framework 1204, probabilities of potential associations for each of the observations 1212 and select, for each of the observations 1212, the potential association with the highest probability.

When observations 1212 are each associated with a particular surgical instrument using probabilistic framework 1204, data 1216 representative of the observations 1212 and the associated surgical instrument may be output for use as input to filter 1206. For example, data 1216 may represent a left observation and the associated surgical instrument and a right observation and the associated surgical instrument, which data 1216 may be output for use as input to filter 1206.

Filter 1206 may receive and use kinematics 1218 for the associated surgical instrument and the data representative of the observations 1212 associated with the surgical instrument to determine and output a physical position 1220 of the surgical instrument at the surgical area. Filter 1206 may determine the physical position 1220 of the surgical instrument based on observations 1212 and kinematics 1218 for the associated surgical instrument in any suitable way, including by using the pair of observations 1212-L and 1212-R as separate and independent input models to filter 1206 to correct kinematics 1218 (e.g., a kinematic-based position) of the associated surgical instrument. This may include using observations 1212-L and 1212-R as stereoscopic images and performing one or more stereo matching operations on observations 1212-L and 1212-R to determine depth of surfaces depicted in observations 1212-L and 1212-R and generate a 3D image-based position (e.g., 3D coordinates or a volume of a 3D box, a sphere, an ellipsoid, etc.) of a surgical instrument as represented by observations 1212-L and 1212-R. Filter 1206 may use the generated image-based 3D image-based position to correct a kinetics-based 3D position of the surgical instrument indicated by kinematics 1218 to determine physical position 1220 in a world 3D space.

In the illustrated example, left endoscopic image 1208-L may be processed independently of right endoscopic image 1208-R by neural network 1202 to determine left observation 1212-L, which may be processed independently of right observation 1212-R to associate a surgical instrument with left observation 1212-L. Similarly, right endoscopic image 1208-R may be processed independently of left endoscopic image 1208-R to determine right observation 1212-R, which may be processed independently of left observation 1212-L to associate a surgical instrument with right observation 1212-R. Left observation 1212-L and right observation 1212-R may be input to filter 1206 (as independent observations) and used by filter 1206 to determine physical position 1220 based on the observations 1212 and kinematics 1218.

Such independent processing of a 2D endoscopic image may conserve computing resources by allowing certain operations of tracking system 600 to be performed using 2D data instead of 3D data to determine an estimated 3D physical position 1220 of a surgical instrument. Moreover, filter 1206 can determine physical position 1220 even when one of the two observations 1212 is unavailable or does not depict a surgical instrument. For example, if a surgical instrument is represented in left endoscopic image 1208-L but not in right endoscopic image 1208-R (e.g., because the surgical instrument is blocked from a right camera view by tissue), both left and right endoscopic images 1208-L and 1208-R may be processed by neural network 1202 to determine observations 1212-L and 1212-R that are associated with a surgical instrument or a false positive and input to filter 1206. Filter 1206 may process both observations 1212-L and 1212-R as input to generate physical position 1220 of the surgical instrument, even though right observation 1212-R is not associated with the surgical instrument. Alternatively, filter 1206 may use only left observation 1212-L and not right observation 1212-R as input when right observation 1212-R is not associated with the surgical instrument by association facility 604 (e.g., because the surgical instrument is within view of a left camera view but is blocked from a right camera view by tissue). Accuracy of the physical position 1220 determined by filter 1206 of the surgical instrument may be maintained for at least some time even though the surgical instrument is temporarily depicted in only one of endoscopic images 1208.

FIG. 12 illustrates an implementation 1200 in which a pair of stereoscopic images 1208-L and 1208-R are input into neural network 1202, which determines a pair of independent observations 1212-L and 1212-R based on the respective stereoscopic images 1208-L and 1208-R. In other implementations, tracking system 600 may be configured to process other forms of endoscopic imagery and/or to determine other observations in other formats, and to use the other observations in other formats to determine a physical position of a surgical instrument. For example, other implementations of system 600 may be configured to process a combination endoscopic image, which may include multiple endoscopic images combined (e.g., stacked) into an aggregate endoscopic image, such as a pair of stereoscopic endoscopic images stacked into a combination image, or a sequence of multiple endoscopic images (e.g., a sequence of two, three, or more video frames) stacked into a combination image. Additionally or alternatively, other implementations of system 600 may be configured to determine an observation that indicates a 3D image-based position of an object of interest depicted in endoscopic imagery.

Figure 13:
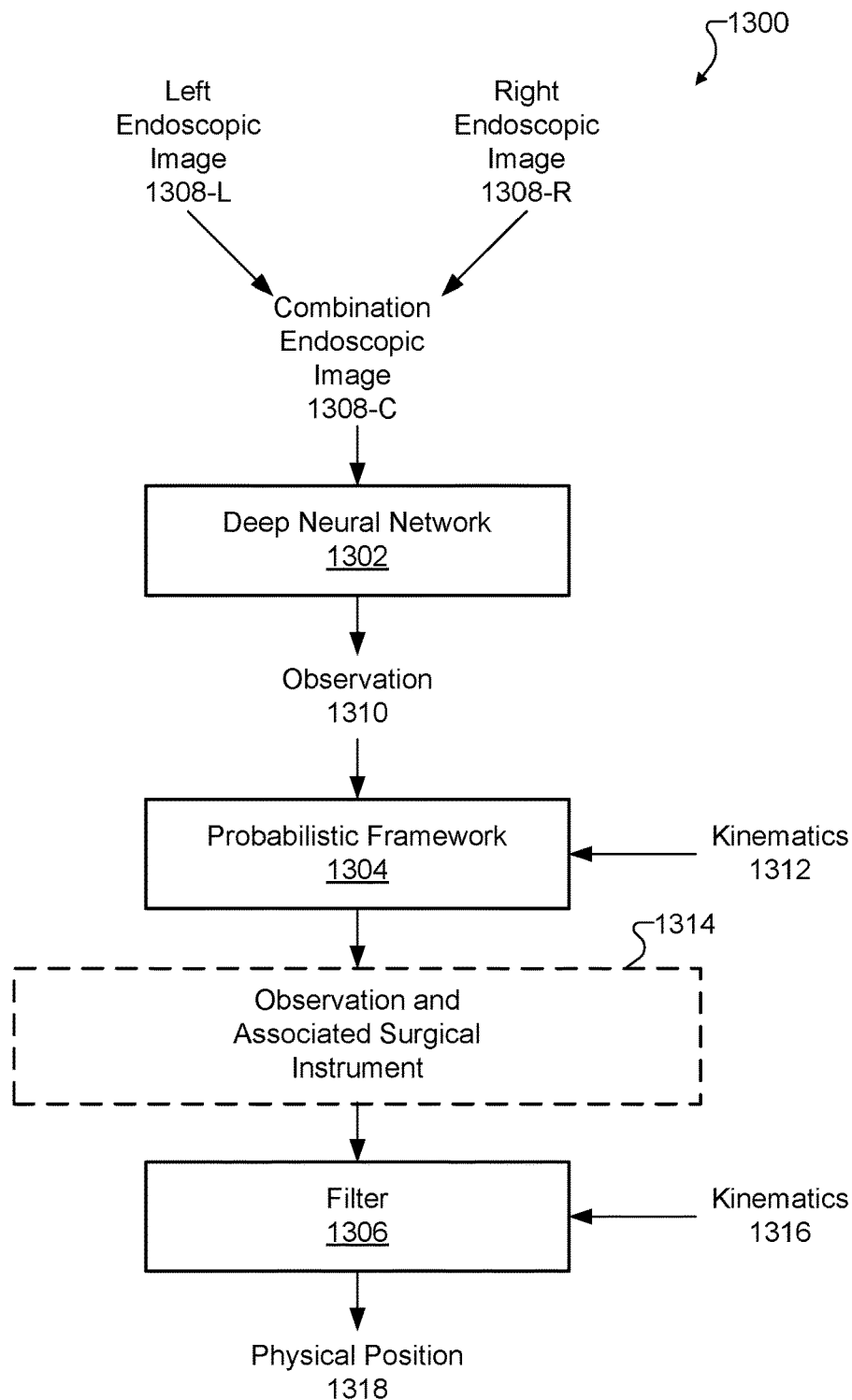

FIG. 13 illustrates an exemplary implementation 1300 that includes a trained neural network 1302, a probabilistic framework 1304, and a filter 1306. In the illustrated example, endoscopic imagery may include a left 2D endoscopic image 1308-L and a right 2D endoscopic image 1308-R that are stereoscopic to one another. Image processing facility 602 may combine endoscopic images 1308-L and 1308-R to form a combination endoscopic image 1308-C. This may be performed in any suitable way, such as by image processing facility 602 stacking endoscopic images 1308-L and 1308-R to form combination endoscopic image 1308-C. If endoscopic images 1308-L and 1308-R each includes a 3-channel RGB image, for example, image processing facility 602 may stack the 3-channel RGB images to form a 6-channel combination image.

Image processing facility 602 may input combination endoscopic image 1308-C into neural network 1302, which may be appropriately configured to determine, based on combination endoscopic image 1308-C, an observation 1310 in any of the ways described herein. In certain examples, neural network 1302 may be configured to determine observation 1310 such that observation 1310 indicates, in 3D space, a 3D image-based position of an object of interest depicted in combination endoscopic image 1308-C (e.g., by performing stereo matching operations to determine depth values for surfaces of the object of interest from combination endoscopic image 1308-C that represents combined stereoscopic images that depict the object of interest).

In alternative implementations, image processing facility 602 may receive endoscopic images 1308-L and 1308-R instead of combination endoscopic image 1308-C and perform stereo matching operations on endoscopic images 1308-L and 1308-R to determine depth values for surfaces of the object of interest from endoscopic images 1308-L and 1308-R. Using the determined depth values, neural network 1302 may determine observation 1310 such that observation 1310 indicates, in 3D space, a 3D image-based position of the object of interest.

Observation 1310 and kinematics 1312 of one or more surgical instruments may then be input to probabilistic framework 1304, which may be used to associate observation 1310 to a particular surgical instrument or a false positive designation based on kinematics 1312, such as by association facility 604 determining, based on kinematics 1312 and using probabilistic framework 1304, probabilities of potential associations for observation 1310 and selecting the association with the highest probability. Because observation 1310 indicates a 3D image-based position of an object of interest in 3D space, association facility 604 may perform certain operations using 3D space data. For example, association facility 604 may analyze the 3D image-based position of the object of interest in 3D space relative to one or more 3D kinematic-based positions of one or more surgical instruments in the 3D space, which 3D kinematic-based positions are indicated by kinematics 1312. Association facility 604 may use results of the analysis (e.g., determined distances) to determine probabilities of potential associations for observation 1310.

When observation 1310 is associated with a particular surgical instrument using probabilistic framework 1304, data 1314 representative of observation 1310 and the associated surgical instrument may be output for use as input to filter 1306. Filter 1306 may access and use kinematics 1316 for the associated surgical instrument and the data 1314 representative of the observation 1310 associated with the surgical instrument to determine and output a physical position 1318 of the surgical instrument at the surgical area. Because observation 1310 indicates a 3D image-based position of an object of interest in 3D space, filter 1306 may perform certain operations using 3D space data. For example, filter 1306 may determine physical position 1318 of the surgical instrument by adjusting a 3D kinematics-based position of the surgical instrument, as indicated by kinematics 1316, with the 3D image-based position of the object of interest, as indicated by observation 1310, to determine a 3D physical position of the surgical instrument in 3D space, such as a global 3D space associated with a robotic surgical system.

By performing certain operations in 3D space, implementation 1300 may determine a highly accurate physical position 1318 of a surgical instrument, particularly with respect the depth of the surgical instrument. Additionally or alternatively, by using a 3D image-based position indicated by observation 1310, implementation 1300 may minimize a number of translations from 2D to 3D space that are performed to determine physical position 1318 of the surgical instrument.

Figure 14:
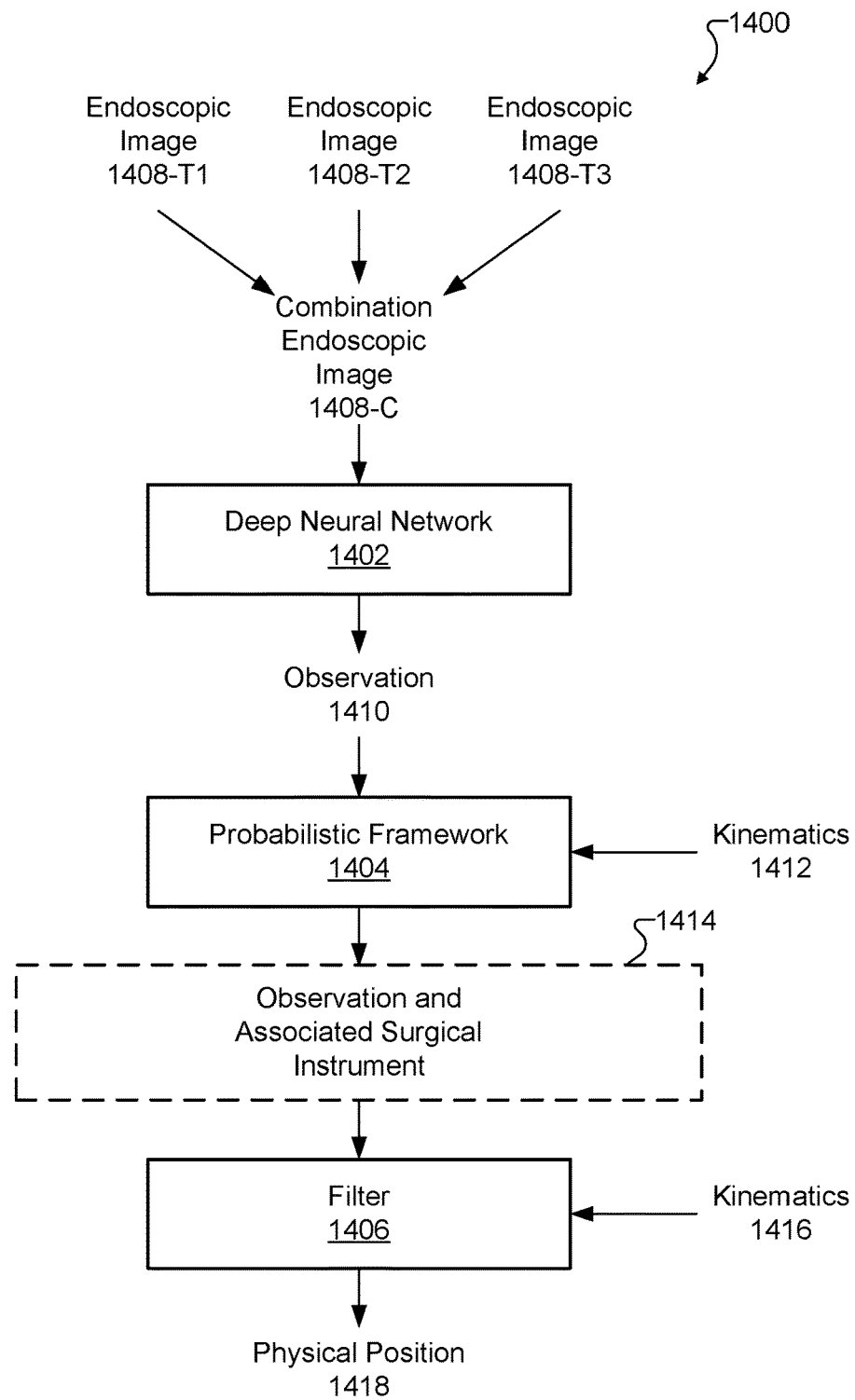

FIG. 14 illustrates an exemplary implementation 1400 that includes a trained neural network 1402, a probabilistic framework 1404, and a filter 1406. In the illustrated example, endoscopic imagery may include a sequence of endoscopic images captured over time (e.g., a sequence of video frames), such as endoscopic images 1408-T1, 1408-T2, and 1408-T3 captured at times T1, T2, and T3. Image processing facility 602 may combine endoscopic images 1408-T1, 1408-T2, and 1408-T3 to form a combination endoscopic image 1408-C. This may be performed in any suitable way, such as by image processing facility 602 stacking endoscopic images 1408-T1, 1408-T2, and 1408-T3 to form combination endoscopic image 1408-C. If endoscopic images 1408-T1, 1408-T2, and 1408-T3 each includes a 3-channel RGB image, for example, image processing facility 602 may stack the 3-channel RGB images to form a 9-channel combination image.

Image processing facility 602 may input combination endoscopic image 1408-C into neural network 1402, which may be appropriately configured to determine, based on combination endoscopic image 1408-C, an observation 1410 in any of the ways described herein. In certain examples, neural network 1402 may be configured to determine observation 1410 such that observation 1410 indicates an image-based position of an object of interest depicted in combination endoscopic image 1408-C. Neural network 1402 may be configured to identify, from combination endoscopic image 1408-C representing a sequence of endoscopic images captured at different times, motion of the object of interest (e.g., velocity, acceleration, etc.) and to use the identified motion to determine the image-based position of the object of interest. In some examples, this may include using the identified motion to determine depth points for a surface of the object of interest and determining a 3D image-based position of the object of interest, which may be particularly useful for estimating depth from a sequence of 2D images captured from the same vantage point (e.g., when a surgical instrument is within the view of only one camera). The use of motion-based cues may contribute to the accuracy of the image-based position of the object of interest. The image-based position of the object of interest may include a 2D or a 3D image-based position, such as described herein.

Observation 1410 and kinematics 1412 of one or more surgical instruments may then be input to probabilistic framework 1404, which may be used to associate observation 1410 to a particular surgical instrument or a false positive designation based on kinematics 1412, such as by association facility 604 determining, based on kinematics 1412 and using probabilistic framework 1404, probabilities of potential associations for observation 1410 and selecting the association with the highest probability.

When observation 1410 is associated with a particular surgical instrument using probabilistic framework 1404, data 1414 representative of observation 1410 and the associated surgical instrument may be output for use as input to filter 1406. Filter 1406 may access and use kinematics 1416 for the associated surgical instrument and the data 1414 representative of the observation 1410 associated with the surgical instrument to determine and output a physical position 1418 of the surgical instrument at the surgical area.

While FIGS. 11-14 illustrate exemplary implementations of tracking system 600 that are configured to process various forms of endoscopic imagery and/or determine various observations, the examples are illustrative. Other implementations may be configured to process other forms of imagery (e.g., other forms of endoscopic imagery and/or non-endoscopic imagery) and/or determine other suitable observations. To this end, a neural network may be appropriately configured to fit a particular implementation.

By using a combination of image-based observations and kinetics of surgical instruments to track surgical instruments, such as described herein, certain technical benefits may be provided by tracking system 600. For example, the precision, accuracy, efficiency, and/or reliability with which surgical instrument are tracked may be improved compared to using only image-based tracking or only kinetic-based tracking. For example, a kinetic-based position indicated by kinetics of a surgical instrument may be used to determine a physical position of a surgical instrument to a certain level of accuracy (e.g., to within approximately one centimeter). By correcting the kinetic-based position of the surgical instrument with an image-based position indicated by an observation as described herein, a physical position of a surgical instrument may be determined and may have an improved level of accuracy (e.g., to within approximately one millimeter).

Figure 15:
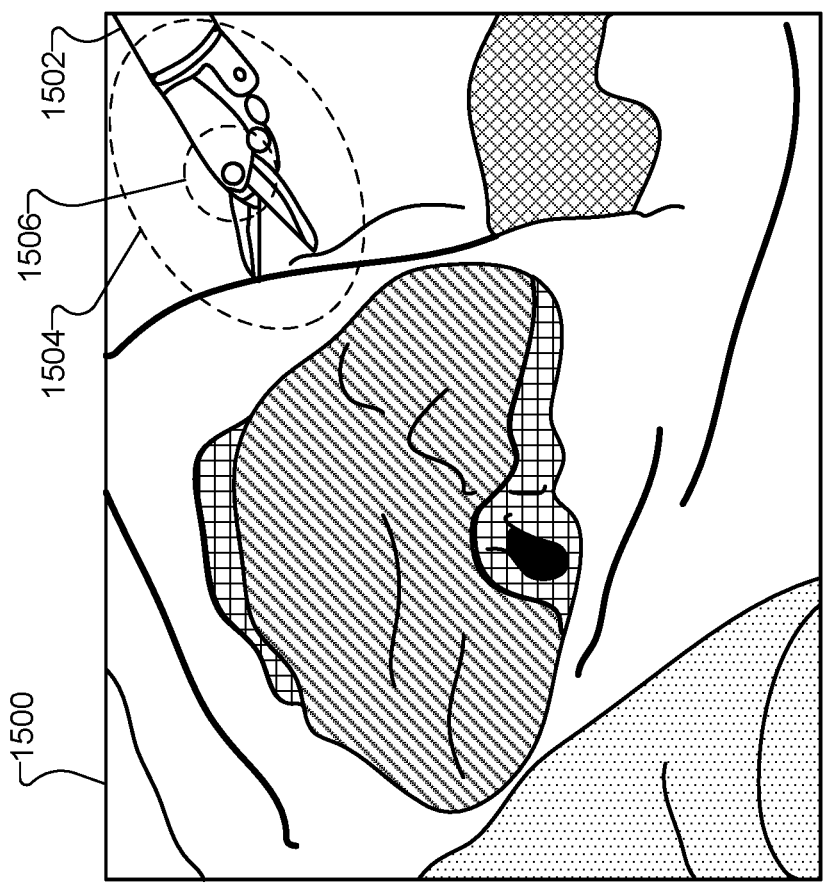
FIG. 15 illustrates an endoscopic image of a surgical area with position indicators overlaid thereon according to principles described herein.

FIG. 15 illustrates an example of such an improved level of accuracy of a determined physical position of a surgical instrument. FIG. 15 shows an endoscopic image 1500 of a surgical area. Endoscopic image 1500 depicts a surgical instrument 1502 located at the surgical area. To illustrate a level of accuracy associated with a physical position of surgical instrument 1502 that is determined based on kinematics only, an indicator 1504 (e.g., an ellipse representing an ellipsoid) is overlaid on endoscopic image 1500 and indicates, by a size of and/or an area covered by indicator 1504, a level of accuracy for a kinematic-based position of surgical instrument 1502. To illustrate an improved level of accuracy associated with a physical position of surgical instrument 1502 determined based on both kinematics and one or more image-based observations, an indicator 1506 (e.g., a circle representing a sphere) is overlaid on endoscopic image 1500 and indicates, by a size of and/or an area covered by indicator 1506, a level of accuracy for the physical position of surgical instrument 1502 determined based on both kinematics and one or more image-based observations such as described herein.

In certain implementations, tracking system 600 may be configured to selectively capture and use endoscopic imagery to track surgical instruments. For example, tracking system 600 may be configured to use kinematics for a surgical instrument to select when to capture and use endoscopic imagery to track the surgical instrument. To illustrate, tracking system 600 may selectively use endoscopic imagery to track the surgical instrument in response to motion of the surgical instrument as indicated by kinematics for the surgical instrument and/or in response to a change in an orientation, angle, position, or other property of an endoscope as indicated by kinematics for the endoscope. Accordingly, tracking system 600 may be configured to toggle between tracking the surgical instrument using kinematics alone without image-based observations and tracking the surgical instrument using kinematics and image-based observations as described herein. Such an implementation may conserve resources (e.g., computing resources, energy, etc.) of tracking system 600 and/or a robotic surgical system.

Tracking of surgical instruments as described herein may provide one or more benefits of a robotic surgical system. For example, tracking of surgical instruments as described herein may facilitate one or more features of a robotic surgical system. In certain implementations, a level of accuracy of physical positions of surgical instruments that are determined as described herein may facilitate certain features of a robotic surgical system that require a high level of accuracy.

As an example, tracking of surgical instruments as described herein may be used by a robotic surgical system to place certain user interface content (e.g., graphics, icons, indicators, etc.) on a display screen relative to a physical position of a surgical instrument or to a physical position of specific tissue that has been touched by the surgical instrument. To illustrate, the robotic surgical system may collocate, on a display screen, user interface content with a visual representation of a surgical instrument in a manner that positions the user interface content proximate to a tip of the surgical instrument without obscuring the surgical instrument from the view of a surgeon or other surgical team member. For example, an indicator may be placed to indicate a mode of operation (e.g., a high-energy mode for cautery) to a surgeon in a manner that makes the indicator readily viewable by the surgeon without requiring the surgeon to look away from the immediate vicinity of the surgical instrument, or an indicator may be placed to indicate specific tissue that has been touched by a probe to help the surgeon see what tissue has already been analyzed by the probe. Such tight placement of user interface content, which may provide benefit to the surgical team and thus to a patient, may be facilitated by accurate determinations of physical locations of the surgical instrument as described herein.

As other examples, tracking of surgical instruments as described herein may be used by a robotic surgical system to warn of or prevent collisions of surgical instruments and/or robotic arms, automate movements of surgical instruments such that the robotic surgical system may control certain movements of surgical instruments (e.g., by automating movement of a probe, such as a cancer probe, to systematically touch surface points of tissue, automating movement of an endoscope, such as based on movement of a surgical tool, etc.), recognize certain tasks being performed during a surgical session (e.g., by recognizing when defined segments of a surgical procedure are being performed), correct inaccuracies of kinematics of surgical instruments, such as inaccuracies introduced by a long kinematic chain and/or flexion of flexible shafts of surgical instruments (e.g., flexible shafts used in a single-port entry system), and calibrate surgical instruments and/or robotic arms (e.g., by moving surgical instruments into a field of view of an endoscope and using information extracted from one or more images of the scene to calibrate the surgical instruments), which may improve a workflow for calibration as compared to traditional calibration techniques. These examples are illustrative only. Tracking of surgical instruments as described herein may be used by a robotic surgical system in any other suitable way.

In certain examples, endoscopic imagery may be used (e.g., by tracking system 600) for camera-arm registration between a camera (e.g., a camera of an endoscope) and a robotic arm that are mounted on separate patient-side systems (e.g., separate patient-side carts). In implementations, such as those described above, in which an endoscope and a surgical instrument are mounted to robotic arms of the same patient-side cart, a kinematic chain connecting the endoscope and the surgical instrument is known, and kinematics of the endoscope and the surgical instrument that are based on the known kinematic chain may be accessed and used by tracking system 600 to track instrument position as described herein. However, in other implementations in which an endoscope and a surgical instrument are mounted to robotic arms of separate, unconnected patient-side carts, there is not a known, complete kinematic chain connecting the endoscope and the surgical instrument because a link in the kinematic chain between the patient-side carts is unknown. That is, the physical relationship between the patient-side carts is unknown and therefore not accessible by tracking system 600. In such an implementation with separate patient-side carts, tracking system 600 may be configured to use endoscopic imagery captured by the endoscope to perform a registration process to register the surgical instrument mounted on one patient-side cart with the endoscope mounted on another patient-side cart with. Tracking system 600 may be configured to perform the registration process once (e.g., as part of a calibration, setup procedure, or other initial registration) and/or periodically or continuously after initial registration to refine the initial registration (e.g., to account for changes in physical positions, which positions may have various kinematic errors) and/or to account for physical adjustments of patient-side cart positions (e.g., an intra-operative adjustment of a patient-side cart).

To perform the registration process, tracking system 600 may determine, based on endoscopic imagery of a surgical area and using a trained neural network, a location of a surgical instrument (e.g., locations of the surgical instrument shaft in left and right endoscopic images). In certain examples, this may include tracking system 600 using a trained neural network to determine an observation for an object of interest depicted in the endoscopic imagery, associating the observation for the object of interest to a surgical instrument in any suitable way (e.g., object recognition), and determining a location (e.g., an image-based location) of the surgical instrument.

Tracking system 600 may then perform a constrained optimization to fit a model of the surgical instrument (e.g., a model of the shaft of the surgical instrument) to the determined location of the surgical instrument (e.g., to the locations of the surgical instrument shaft in the left and right endoscopic images). Tracking system 600 may be configured to constrain the optimization to search only for solutions that are rotations and translations on the plane of the floor on which the patient-side carts are placed. This constrained optimization may provide faster and/or more accurate results than a traditional optimization performed in all six degrees of freedom.

Tracking system 600 may perform the registration process for one surgical instrument at a time or for multiple instruments concurrently. If a single surgical instrument is mounted on a single patient-side cart and/or is installed or registered alone, association of an observation to the surgical instrument may be straightforward. If two or more surgical instruments are each mounted on a separate patient-side cart and/or are installed or registered concurrently, tracking system 600 may be configured to associate observations determined from endoscopic imagery to surgical instruments in any suitable way, including by using a probabilistic framework as described herein.

The registration process may be used by tracking system 600 to determine a missing link in a kinematic chain connecting an endoscope and a surgical instrument that are mounted on separate patient-side carts. Tracking system 600 may represent the missing link as a transform that defines an estimated physical relationship between the patient-side carts. The transform may define a rotation and a translation that may be applied to convert data points from a reference frame of one patient-side cart to a reference frame of another patient-side cart (e.g., to convert coordinate points from a coordinate system of one patient-side cart to a coordinate system of another patient-side cart) and vice versa.

Tracking system 600 may use the missing link to complete a kinematic chain connecting an endoscope and a surgical instrument that are mounted on separate patient-side carts such that the complete kinematic chain is known and accessible to tracking system 600. Tracking system 600 may then use kinematics of the endoscope and/or surgical instrument to track the position of the surgical instrument as described herein. For example, tracking system 600 may use endoscopic imagery as described herein to correct a kinematic position of the surgical instrument.

In certain examples, the use of a neural network as descried herein may provide one or more advantages over conventional computer vision techniques. For example, the use of a neural network to determine an observation for an object of interest depicted in endoscopic imagery, as described herein, may be significantly faster and/or more accurate than conventional computer vision techniques (e.g., traditional pure vision approaches in which algorithms that extract specific features from imagery are hand-engineered). Certain implementations of a neural network to determine an observation for a distal clevis of a surgical instrument have been found to be approximately ten times as fast as a conventional marker-based computer vision technique (e.g., speeds of 10 Hz compared to 1 Hz).

A neural network, as used herein, may include an input layer, any suitable number of hidden layers, and an output layer. In exemplary implementations in which multiple hidden layers are included in a neural network, the multiple hidden layers may be layered in any suitable way. A neural network that includes multiple hidden layers may be referred to as a "deep neural network."

While exemplary implementations that include and/or use a neural network are described herein, alternative implementations may use other suitable machine learning models configured to learn ways to extract specific features from endoscopic imagery for object detection and/or classification.

Figure 16:
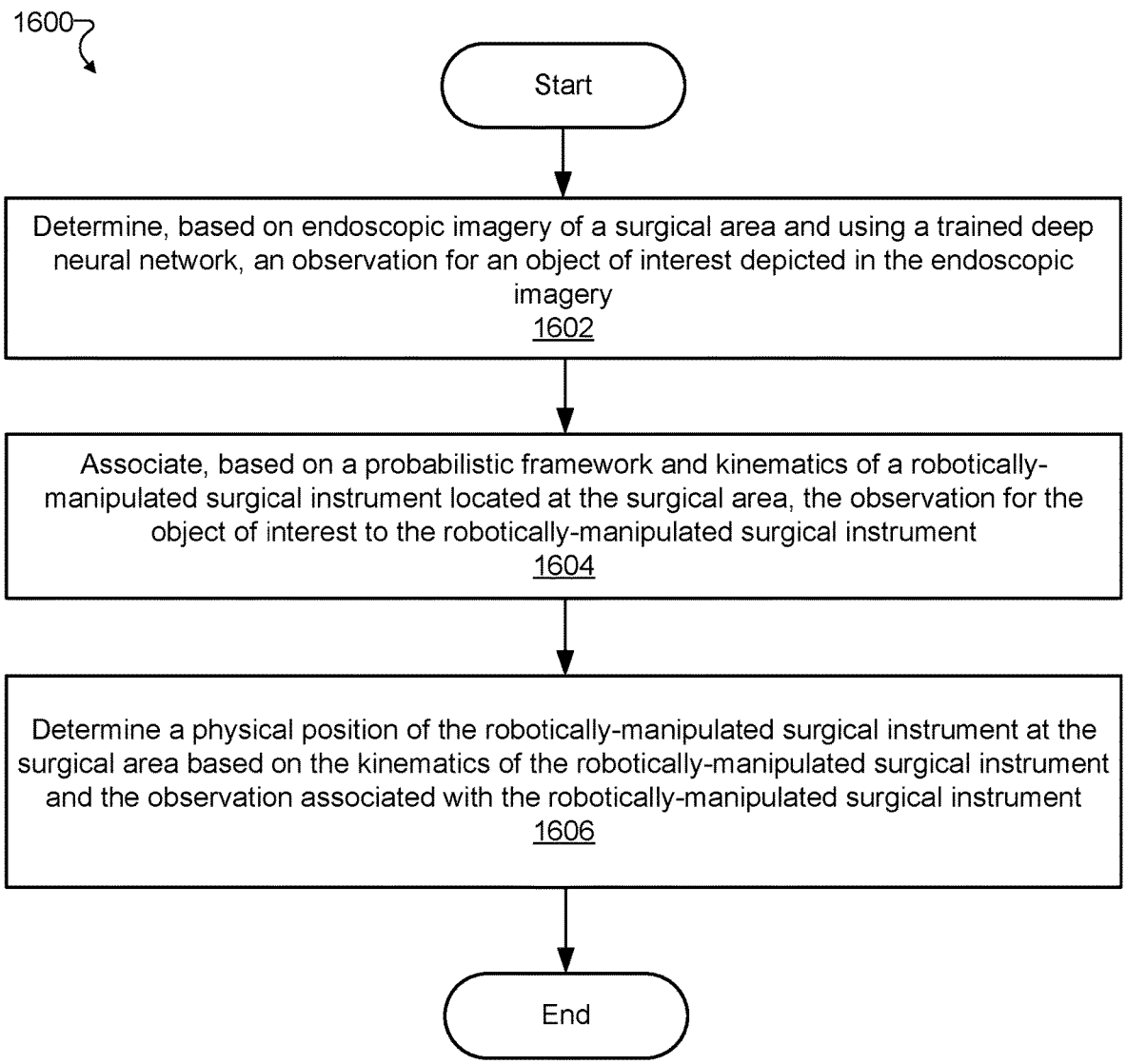
FIGS. 16-17 illustrate exemplary methods of tracking a surgical instrument according to principles described herein.

FIG. 16 illustrates an exemplary method 1600 of tracking a position of a robotically-manipulated surgical instrument. While FIG. 16 illustrates exemplary operations according to one embodiment, other embodiments may omit, add to, reorder, and/or modify any of the operations shown in FIG. 16. One or more of the operations shown in FIG. 16 may be performed by a tracking system such as system 600, any components included therein, and/or any implementation thereof.

In operation 1602, a tracking system may determine, based on endoscopic imagery of a surgical area and using a trained neural network, an observation for an object of interest depicted in the endoscopic imagery. Operation 1602 may be performed in any of the ways described herein.

In operation 1604, the tracking system may associate, based on a probabilistic framework and kinematics of a robotically-manipulated surgical instrument located at the surgical area, the observation for the object of interest to the robotically-manipulated surgical instrument. Operation 1604 may be performed in any of the ways described herein.

In operation 1606, the tracking system may determine a physical position of the robotically-manipulated surgical instrument at the surgical area based on the kinematics of the robotically-manipulated surgical instrument and the observation associated with the robotically-manipulated surgical instrument. Operation 1606 may be performed in any of the ways described herein.

Figure 17:
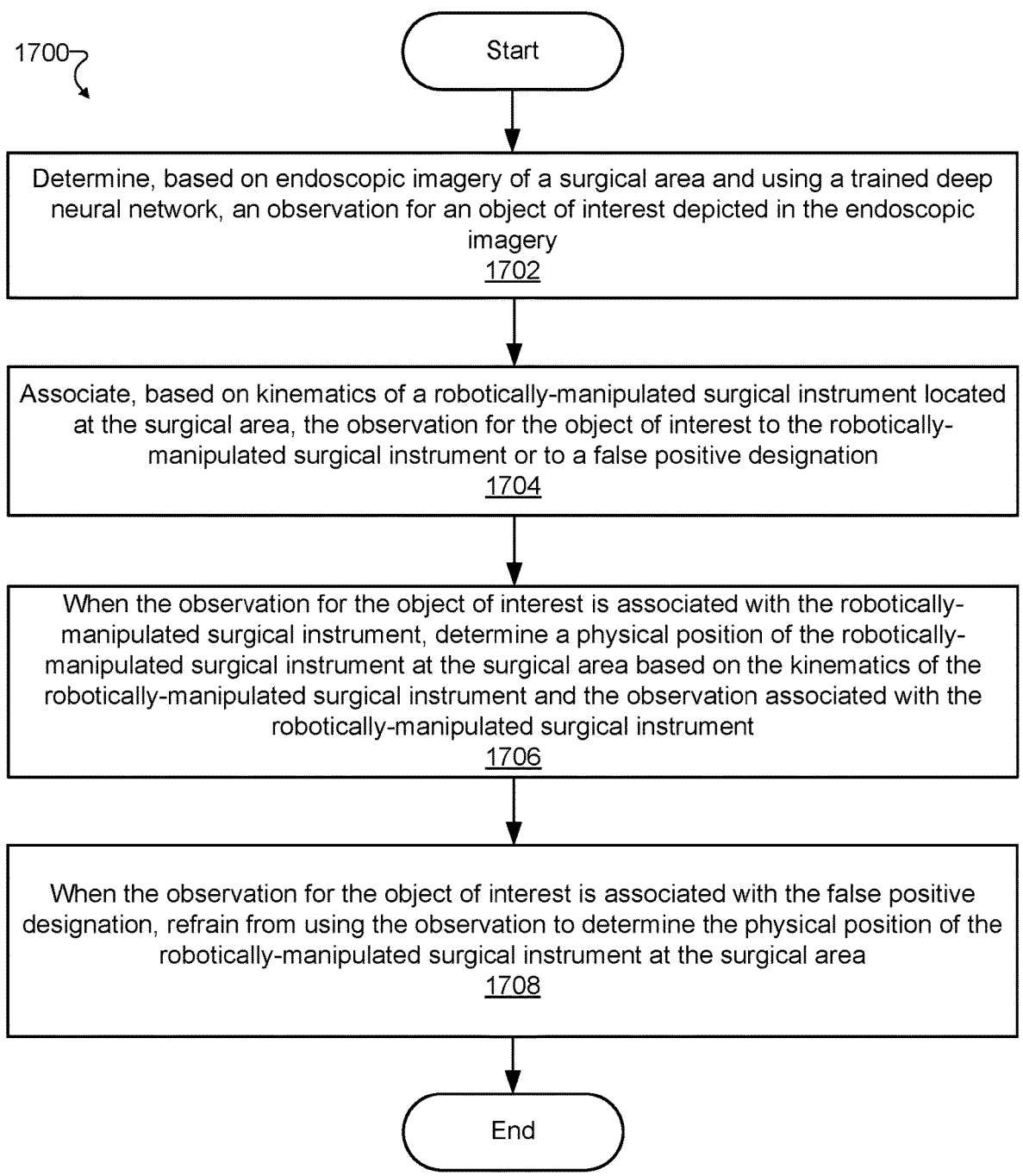

FIG. 17 illustrates another exemplary method 1700 of tracking a position of a robotically-manipulated surgical instrument. While FIG. 17 illustrates exemplary operations according to one embodiment, other embodiments may omit, add to, reorder, and/or modify any of the operations shown in FIG. 17. One or more of the operations shown in FIG. 17 may be performed by a tracking system such as system 600, any components included therein, and/or any implementation thereof.

In operation 1702, a tracking system may determine, based on endoscopic imagery of a surgical area and using a trained neural network, an observation for an object of interest depicted in the endoscopic imagery. Operation 1702 may be performed in any of the ways described herein.

In operation 1704, the tracking system may associate, based on kinematics of a robotically-manipulated surgical instrument located at the surgical area, the observation for the object of interest to the robotically-manipulated surgical instrument or a false positive designation. Operation 1704 may be performed in any of the ways described herein.

In operation 1706, when the observation for the object of interest is associated with the robotically-manipulated surgical instrument in operation 1704, the tracking system may determine a physical position of the robotically-manipulated surgical instrument at the surgical area based on the kinematics of the robotically-manipulated surgical instrument and the observation associated with the robotically-manipulated surgical instrument. Operation 1706 may be performed in any of the ways described herein.

In operation 1708, when the observation for the object of interest is associated with the false positive designation in operation 1704, the tracking system may refrain from using the observation to determine the physical position of the robotically-manipulated surgical instrument at the surgical area. Operation 1706 may be performed in any of the ways described herein.

In certain embodiments, one or more of the systems, components, and/or processes described herein may be implemented and/or performed by one or more appropriately configured computing devices. To this end, one or more of the systems and/or components described above may include or be implemented by any computer hardware and/or computer-implemented instructions (e.g., software) embodied on at least one non-transitory computer-readable medium configured to perform one or more of the processes described herein. In particular, system components may be implemented on one physical computing device or may be implemented on more than one physical computing device. Accordingly, system components may include any number of computing devices, and may employ any of a number of computer operating systems.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a compact disc read-only memory ("CD-ROM"), a digital video disc ("DVD"), any other optical medium, random access memory ("RAM"), programmable read-only memory ("PROM"), electrically erasable programmable read-only memory ("EPROM"), FLASH-EEPROM, any other memory chip or cartridge, or any other tangible medium from which a computer can read.

Figure 18:
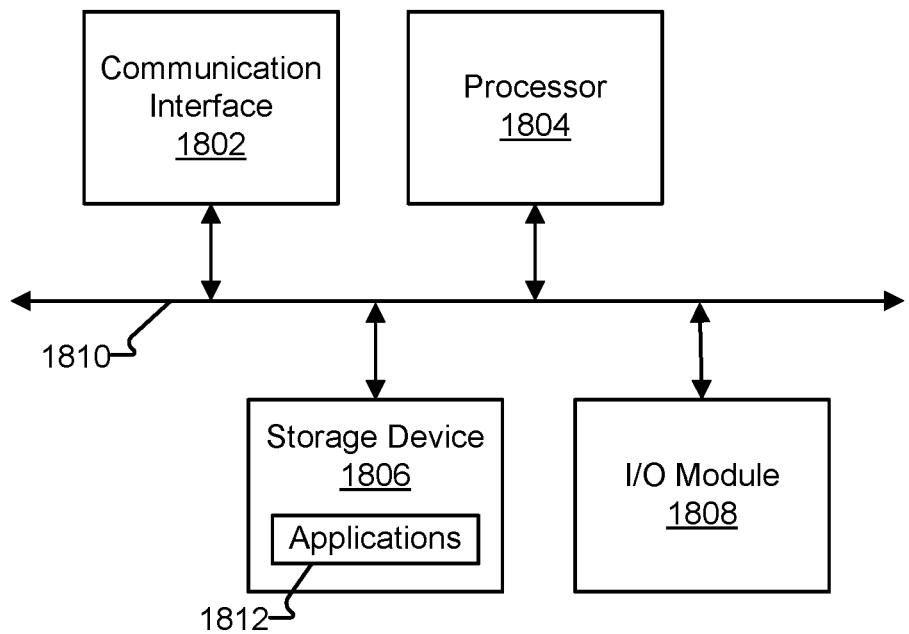
FIG. 18 illustrates an exemplary computing system according to principles described herein.

FIG. 18 illustrates an exemplary computing device 1800 that may be specifically configured to perform one or more of the processes described herein. As shown in FIG. 18, computing device 1800 may include a communication interface 1802, a processor 1804, a storage device 1806, and an input/output ("I/O") module 1808 communicatively connected via a communication infrastructure 1810. While an exemplary computing device 1800 is shown in FIG. 18, the components illustrated in FIG. 18 are not intended to be limiting. Additional or alternative components may be used in other embodiments. Components of computing device 1800 shown in FIG. 18 will now be described in additional detail.

Communication interface 1802 may be configured to communicate with one or more computing devices. Examples of communication interface 1802 include, without limitation, a wired network interface (such as a network interface card), a wireless network interface (such as a wireless network interface card), a modem, an audio/video connection, and any other suitable interface.

Processor 1804 generally represents any type or form of processing unit capable of processing data or interpreting, executing, and/or directing execution of one or more of the instructions, processes, and/or operations described herein. Processor 1804 may direct execution of operations in accordance with one or more applications 1812 or other computer-executable instructions such as may be stored in storage device 1806 or another computer-readable medium.

Storage device 1806 may include one or more data storage media, devices, or configurations and may employ any type, form, and combination of data storage media and/or device. For example, storage device 1806 may include, but is not limited to, a hard drive, network drive, flash drive, magnetic disc, optical disc, RAM, dynamic RAM, other non-volatile and/or volatile data storage units, or a combination or sub-combination thereof. Electronic data, including data described herein, may be temporarily and/or permanently stored in storage device 1806. For example, data representative of one or more executable applications 1812 configured to direct processor 1804 to perform any of the operations described herein may be stored within storage device 1806. In some examples, data may be arranged in one or more databases residing within storage device 1806.

I/O module 1808 may include one or more I/O modules configured to receive user input and provide user output. One or more I/O modules may be used to receive input for a single virtual reality experience. I/O module 1808 may include any hardware, firmware, software, or combination thereof supportive of input and output capabilities. For example, I/O module 1808 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1808 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1808 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 1800. For example, one or more applications 1812 residing within storage device 1806 may be configured to direct processor 1804 to perform one or more processes or functions associated facilities 602 through 606 of system 600. Likewise, storage facility 608 of system 600 may be implemented by storage device 1806 or a component thereof.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A surgical instrument tracking system comprising:
a memory storing instructions;
a processor communicatively coupled to the memory and configured to execute the instructions to:
   determine, based on imagery of a surgical area, an observation for an object of interest depicted in the imagery;
   determine a probability of an association of the observation to a robotically-manipulated surgical instrument located at the surgical area based on kinematics of the robotically-manipulated surgical instrument;
   associate the observation for the object of interest to the robotically-manipulated surgical instrument based on the probability; and
   determine a physical position of the robotically-manipulated surgical instrument at the surgical area based on the kinematics of the robotically-manipulated surgical instrument and the observation associated with the robotically-manipulated surgical instrument.

2. The system of claim 1, wherein:
the imagery comprises a left endoscopic image and a right endoscopic image that is stereoscopic with the left endoscopic image;
the observation for the object of interest comprises a left observation and a right observation for the object of interest; and
the processor is configured to execute the instructions to:
   determine the observation for the object of interest by using a trained neural network to determine the left observation for the object of interest based on the left endoscopic image and to determine the right observation for the object of interest based on the right endoscopic image;
   associate the observation for the object of interest to the robotically-manipulated surgical instrument by associating the left observation to the robotically-manipulated surgical instrument and associating the right observation to the robotically-manipulated surgical instrument; and
   determine the physical position of the robotically-manipulated surgical instrument at the surgical area by using the left observation and the right observation to determine a three-dimensional ("3D") position of the object of interest in a 3D space and adjusting a 3D kinematic-based position of the robotically-manipulated surgical instrument in the 3D space based on the 3D position of the object of interest in the 3D space.

3. The system of claim 1, wherein:
the imagery comprises a left endoscopic image and a right endoscopic image that is stereoscopic with the left endoscopic image; and
the processor is configured to execute the instructions to stereo match the left and right endoscopic images and determine the observation for the object of interest by using a trained neural network to determine the observation for the object of interest based on the stereo matched left and right endoscopic images.

4. The system of claim 1, wherein:
the imagery comprises a combination endoscopic image; and
the processor is configured to execute the instructions to:
generate the combination endoscopic image by combining a first endoscopic image and a second endoscopic image that is stereoscopic to the first endoscopic image;
determine the observation for the object of interest by using a trained neural network to determine, based on the combination endoscopic image, a three-dimensional ("3D") image-based position of the object of interest in a 3D space; and
determine the physical position of the robotically-manipulated surgical instrument at the surgical area by adjusting a 3D kinematic-based position of the robotically-manipulated surgical instrument in the 3D space based on the 3D image-based position of the object of interest in the 3D space.

5. The system of claim 1, wherein:
the imagery comprises a combination endoscopic image; and
the processor is configured to execute the instructions to:
generate the combination endoscopic image by combining multiple endoscopic images included in a sequence of endoscopic video frames;
determine the observation for the object of interest by using a trained neural network to determine, based on the combination endoscopic image, a three-dimensional ("3D") image-based position of the object of interest in a 3D space; and
determine the physical position of the of the robotically-manipulated surgical instrument at the surgical area by adjusting a 3D kinematic-based position of the robotically-manipulated surgical instrument in the 3D space based on the 3D image-based position of the object of interest in the 3D space.

6. The system of claim 5, wherein the processor is configured to execute the instructions to determine, based on the combination endoscopic image, the 3D image-based position of the object of interest in the 3D space based at least in part on a motion of the object of interest identified from the combination endoscopic image.

7. The system of claim 1, wherein the processor is configured to execute the instructions to determine the physical position of the robotically-manipulated surgical instrument at the surgical area by adjusting a kinematic-based position of the robotically-manipulated surgical instrument based on an image-based position of the object of interest indicated by the observation.

8. The system of claim 1, wherein the processor is configured to execute the instructions to:
determine, based on the imagery of the surgical area, an additional observation for an additional object of interest depicted in the imagery;
determine a probability of an association of the additional observation to the robotically-manipulated surgical instrument located at the surgical area based on the kinematics of the robotically-manipulated surgical instrument;
associate the additional observation for the additional object of interest to a false positive designation based on the probability of the association of the additional observation to the robotically-manipulated surgical instrument; and refrain from using the additional observation for the additional object of interest to determine the physical position of the robotically-manipulated surgical instrument.

9. The system of claim 1, wherein the processor is configured to execute the instructions to associate the observation for the object of interest to the robotically-manipulated surgical instrument by:
determining a first probability for an association of the observation for the object of interest to the robotically-manipulated surgical instrument;
determining a second probability for an association of the observation for the object of interest to a false positive designation;
determining that the first probability is higher than the second probability; and
associating the observation for the object of interest to the robotically-manipulated surgical instrument in response to the determining that the first probability is higher than the second probability.

10. The system of claim 1, wherein the processor is configured to execute the instructions to:
determine, based on the imagery of the surgical area, an additional observation for an additional object of interest depicted in the imagery;
determine a probability of an association of the additional observation to the robotically-manipulated surgical instrument located at the surgical area based on the kinematics of the robotically-manipulated surgical instrument;
associate the additional observation for the additional object of interest to a false positive designation based on the probability of the association of the additional observation to the robotically-manipulated surgical instrument; and
wherein the processor is configured to execute the instructions to associate the observation for the object of interest to the robotically-manipulated surgical instrument and associate the additional observation for the additional object of interest to the false positive designation by:
determining a first probability for a first set of associations that includes an association of the observation for the object of interest to the robotically-manipulated surgical instrument and an association of the additional observation for the additional object of interest to the false positive designation;
determining a second probability for a second set of associations that includes an association of the observation for the object of interest to the false positive designation and an association of the additional observation for the additional object of interest to the robotically-manipulated surgical instrument;
determining that the first probability is higher than the second probability; and
associating the observation for the object of interest to the robotically-manipulated surgical instrument and associating the additional observation for the additional object of interest to the false positive designation in response to the determining that the first probability is higher than the second probability.

11. The system of claim 1, wherein the observation for the object of interest indicates an image-based position of the object of interest and an additional attribute associated with the object of interest.

12. The system of claim 11, wherein the additional attribute associated with the object of interest comprises one of:
  a type of surgical instrument associated with the object of interest;
  an orientation associated with the object of interest; and
  a motion cue associated with the object of interest.

13. The system of claim 1, wherein the processor is configured to execute the instructions to output data representative of the physical position for use by a robotic surgical system to display user interface content collocated with a visual representation of the robotically-manipulated surgical instrument displayed on a display screen.

14. A surgical instrument tracking system comprising:
  a memory storing instructions;
  a processor communicatively coupled to the memory and configured to execute the instructions to:
    determine, based on endoscopic imagery of a surgical area and using a trained neural network, an observation for an object of interest depicted in the endoscopic imagery;
    determine a probability of an association of the observation to a robotically-manipulated surgical instrument located at the surgical area based on kinematics of the robotically-manipulated surgical instrument;
    associate, based on the probability, the observation for the object of interest to the robotically-manipulated surgical instrument or to a false positive designation;
    when the observation for the object of interest is associated with the robotically-manipulated surgical instrument, determine a physical position of the robotically-manipulated surgical instrument at the surgical area by adjusting a kinematic-based position of the robotically-manipulated surgical instrument based on an image-based position of the observation associated with the robotically-manipulated surgical instrument; and
    when the observation for the object of interest is associated with the false positive designation, refrain from using the observation to determine the physical position of the robotically-manipulated surgical instrument at the surgical area.

15. A method comprising:
  determining, by a surgical instrument tracking system, based on imagery of a surgical area, an observation for an object of interest depicted in the imagery;
  determining, by the surgical instrument tracking system, a probability of an association of the observation to a robotically-manipulated surgical instrument located at the surgical area based on kinematics of the robotically-manipulated surgical instrument;
  associating, by the surgical instrument tracking system, the observation for the object of interest to the robotically-manipulated surgical instrument based on the probability; and
  determining, by the surgical instrument tracking system, a physical position of the robotically-manipulated surgical instrument at the surgical area based on the kinematics of the robotically-manipulated surgical instrument and the observation associated with the robotically-manipulated surgical instrument.

16. The method of claim 15, wherein:
  the determining of the observation for the object of interest comprises using a trained neural network to determine a left observation for the object of interest based on a left image included in the imagery and to determine a right observation for the object of interest based on a right image included in the imagery;
  the associating of the observation for the object of interest to the robotically-manipulated surgical instrument comprises associating the left observation to the robotically-manipulated surgical instrument and associating the right observation to the robotically-manipulated surgical instrument; and
  the determining of the physical position of the robotically-manipulated surgical instrument at the surgical area comprises using the left observation and the right observation to determine a three-dimensional ("3D") position of the object of interest in a 3D space and adjusting a 3D kinematic-based position of the robotically-manipulated surgical instrument in the 3D space based on the 3D position of the object of interest in the 3D space.

17. The method of claim 15, wherein:
  the determining of the observation for the object of interest comprises using a trained neural network to determine, based on a combination image that is included in the imagery and that is formed by combining a first image and a second image that is stereoscopic to the first image, a three-dimensional ("3D") image-based position of the object of interest in a 3D space; and
  the determining of the physical position of the robotically-manipulated surgical instrument at the surgical area comprises adjusting a 3D kinematic-based position of the robotically-manipulated surgical instrument in the 3D space based on the 3D image-based position of the object of interest in the 3D space.

18. The method of claim 15, wherein:
  the determining of the observation for the object of interest comprises using a trained neural network to determine, based on a combination image that is included in the imagery and that is formed by combining a sequence of video frames, a three-dimensional ("3D") image-based position of the object of interest in a 3D space; and
  the determining of the physical position of the robotically-manipulated surgical instrument at the surgical area comprises adjusting a 3D kinematic-based position of the robotically-manipulated surgical instrument in the 3D space based on the 3D image-based position of the object of interest in the 3D space.

19. The method of claim 15, wherein the determining of the physical position of the robotically-manipulated surgical instrument at the surgical area comprises adjusting a kinematic-based position of the robotically-manipulated surgical instrument based on an image-based position of the object of interest indicated by the observation.

20. The method of claim 15, further comprising registering, based on the imagery, the robotically-manipulated surgical instrument, which is mounted on a first cart, with an endoscope that captures the imagery, the endoscope mounted on a second cart that is separate from the first cart, the registering comprising determining a physical relationship between the first cart and the second cart.

* * * * *